(12) United States Patent
Downey et al.

(10) Patent No.: US 12,357,337 B2
(45) Date of Patent: Jul. 15, 2025

(54) SYSTEM AND METHOD FOR DRIVING AN ULTRASONIC HANDPIECE AS A FUNCTION OF THE MECHANICAL IMPEDANCE OF THE HANDPIECE

(71) Applicant: Stryker Corporation, Kalamazoo, MI (US)

(72) Inventors: Adam Downey, Kalamazoo, MI (US); Matthew Owen, Vicksburg, MI (US)

(73) Assignee: Stryker Corporation, Portage, MI (US)

( * ) Notice: Subject to any disclaimer, the term of this patent is extended or adjusted under 35 U.S.C. 154(b) by 167 days.

(21) Appl. No.: 18/227,412

(22) Filed: Jul. 28, 2023

(65) Prior Publication Data

US 2023/0363784 A1 Nov. 16, 2023

Related U.S. Application Data

(63) Continuation of application No. 17/096,293, filed on Nov. 12, 2020, now Pat. No. 11,712,260, which is a continuation of application No. 15/981,986, filed on May 17, 2018, now Pat. No. 10,864,011, which is a continuation of application No. 15/014,412, filed on
(Continued)

(51) Int. Cl.
| | |
|---|---|
| *A61B 17/32* | (2006.01) |
| *A61B 17/14* | (2006.01) |
| *A61B 17/00* | (2006.01) |
| *A61B 18/00* | (2006.01) |

(52) U.S. Cl.
CPC .... *A61B 17/320068* (2013.01); *A61B 17/142* (2016.11); *A61B 2017/0003* (2013.01); *A61B 2017/00977* (2013.01); *A61B 2017/320069* (2017.08); *A61B 2017/32007* (2017.08); *A61B 2018/00648* (2013.01); *A61B 2018/0072* (2013.01); *A61B 2018/00732* (2013.01); *A61B 2018/00833* (2013.01); *A61B 2018/00892* (2013.01); *A61B 2018/00988* (2013.01)

(58) Field of Classification Search
CPC . A61B 17/32; A61B 17/320068; A61B 17/14; A61B 17/142; A61B 17/05; B06B 1/00; B06B 3/00; G10K 11/00
See application file for complete search history.

(56) References Cited

U.S. PATENT DOCUMENTS

| | | | |
|---|---|---|---|
| 3,900,823 | A | 8/1975 | Sokal et al. |
| 4,562,413 | A | 12/1985 | Mishiro et al. |

(Continued)

FOREIGN PATENT DOCUMENTS

| | | |
|---|---|---|
| CA | 2359426 C | 6/2010 |
| CA | 2359742 C | 9/2010 |

(Continued)

OTHER PUBLICATIONS

English language abstract for KR 2017-0039726 A extracted from espacenet.com database on Jan. 17, 2024, 2 pages.
(Continued)

*Primary Examiner* — Christopher J Beccia
(74) *Attorney, Agent, or Firm* — Howard & Howard Attorneys PLLC

(57) ABSTRACT

An ultrasonic surgical tool system for actuating a handpiece with a tip. The frequency of the drive signal applied to the handpiece drivers is a function of the equivalent of current through the mechanical components of the handpiece and tip and the frequency responsiveness of these components.

18 Claims, 15 Drawing Sheets

Related U.S. Application Data

Feb. 3, 2016, now Pat. No. 10,016,209, which is a continuation of application No. PCT/US2014/050034, filed on Aug. 7, 2014.

(60) Provisional application No. 61/863,152, filed on Aug. 7, 2013.

(56) References Cited

U.S. PATENT DOCUMENTS

| | | |
|---|---|---|
| 4,852,578 A | 8/1989 | Companion et al. |
| 5,184,605 A | 2/1993 | Grzeszykowski |
| 5,836,897 A | 11/1998 | Sakurai et al. |
| 6,066,135 A | 5/2000 | Honda |
| 6,205,855 B1 | 3/2001 | Pfeiffer |
| 6,233,476 B1 | 5/2001 | Strommer et al. |
| 6,569,109 B2 | 5/2003 | Sakurai et al. |
| 6,585,745 B2 | 7/2003 | Cimino |
| 6,695,847 B2 | 2/2004 | Bianchetti et al. |
| 6,908,472 B2 | 6/2005 | Wiener et al. |
| 7,077,820 B1 | 7/2006 | Kadziauskas et al. |
| 7,179,271 B2 | 2/2007 | Friedman et al. |
| 7,316,664 B2 | 1/2008 | Kadziauskas et al. |
| 7,335,997 B2 | 2/2008 | Wiener |
| 7,554,343 B2 | 6/2009 | Bromfield |
| 7,655,003 B2 | 2/2010 | Lorang et al. |
| 7,749,240 B2 | 7/2010 | Takahashi et al. |
| 7,794,414 B2 | 9/2010 | Rabiner et al. |
| 7,811,255 B2 | 10/2010 | Boukhny et al. |
| 7,821,143 B2 | 10/2010 | Wiener |
| 7,938,120 B2 | 5/2011 | Kadziauskas et al. |
| 8,002,783 B2 | 8/2011 | Vercellotti et al. |
| 8,016,843 B2 | 9/2011 | Escaf |
| 8,020,565 B2 | 9/2011 | Kadziauskas et al. |
| 8,115,366 B2 | 2/2012 | Hoffman et al. |
| 8,197,502 B2 | 6/2012 | Smith et al. |
| 8,231,564 B2 | 7/2012 | Kadziauskas et al. |
| 8,236,020 B2 | 8/2012 | Smith et al. |
| 8,252,012 B2 | 8/2012 | Stulen |
| 8,253,303 B2 | 8/2012 | Giordano et al. |
| 8,257,307 B2 | 9/2012 | Boukhny et al. |
| 8,372,100 B2 | 2/2013 | Yamada |
| 8,512,325 B2 | 8/2013 | Mathonnet |
| 8,545,528 B2 | 10/2013 | Rob et al. |
| 8,653,919 B2 | 2/2014 | Culp et al. |
| 8,659,208 B1 | 2/2014 | Rose et al. |
| 8,709,031 B2 | 4/2014 | Stulen |
| 8,779,648 B2 | 7/2014 | Giordano et al. |
| 8,852,138 B2 | 10/2014 | Kadzlauskas et al. |
| 8,887,735 B2 | 11/2014 | Kadzlauskas et al. |
| 8,945,162 B2 | 2/2015 | Kadziauskas et al. |
| 9,060,775 B2 | 6/2015 | Wiener et al. |
| 9,060,776 B2 | 6/2015 | Yates et al. |
| 9,072,539 B2 | 7/2015 | Messerly et al. |
| 9,089,360 B2 | 7/2015 | Messerly et al. |
| 9,220,483 B2 | 12/2015 | Frankhouser et al. |
| 9,504,855 B2 | 11/2016 | Messerly et al. |
| 9,572,711 B2 | 2/2017 | Raney et al. |
| 9,603,609 B2 | 3/2017 | Kawashima et al. |
| 9,707,127 B2 | 7/2017 | Kadziauskas et al. |
| 9,795,808 B2 | 10/2017 | Messerly et al. |
| 9,845,162 B2 | 12/2017 | Campbell, Jr. |
| 9,943,326 B2 | 4/2018 | Ross et al. |
| 10,016,209 B2 | 7/2018 | Downey et al. |
| 10,022,567 B2 | 7/2018 | Messerly et al. |
| 10,022,568 B2 | 7/2018 | Messerly et al. |
| 10,194,972 B2 | 2/2019 | Yates et al. |
| 10,265,117 B2 | 4/2019 | Wiener et al. |
| 10,335,614 B2 | 7/2019 | Messerly et al. |
| 10,376,305 B2 | 8/2019 | Yates et al. |
| 10,687,840 B1 | 6/2020 | Cotter et al. |
| 10,765,557 B2 | 9/2020 | Kadziauskas et al. |
| 10,820,912 B2 | 11/2020 | Wildgen et al. |
| 10,864,011 B2 | 12/2020 | Downey et al. |
| 11,617,598 B2 | 4/2023 | Downey et al. |
| 11,712,260 B2 | 8/2023 | Downey et al. |
| 2003/0163129 A1 | 8/2003 | Lee et al. |
| 2003/0164658 A1 | 9/2003 | Saraf |
| 2003/0199794 A1 | 10/2003 | Sakurai et al. |
| 2005/0113819 A1 | 5/2005 | Wham et al. |
| 2005/0188743 A1 | 9/2005 | Land |
| 2008/0004608 A1 | 1/2008 | Dacquay et al. |
| 2008/0234712 A1 | 9/2008 | Tanaka |
| 2010/0102672 A1 | 4/2010 | Hoffman et al. |
| 2010/0125292 A1 | 5/2010 | Wiener et al. |
| 2011/0087256 A1 | 4/2011 | Wiener et al. |
| 2012/0078139 A1 | 3/2012 | Aldridge et al. |
| 2012/0221031 A1 | 8/2012 | Smith et al. |
| 2013/0072853 A1 | 3/2013 | Wong et al. |
| 2017/0071621 A1 | 3/2017 | Downey et al. |
| 2018/0263652 A1 | 9/2018 | Downey et al. |
| 2018/0368878 A1 | 12/2018 | Tanigami et al. |
| 2019/0038297 A1 | 2/2019 | Briscoe |
| 2019/0175208 A1 | 6/2019 | Ross et al. |
| 2019/0274706 A1 | 9/2019 | Nott et al. |
| 2019/0274707 A1 | 9/2019 | Sawhney et al. |
| 2019/0274710 A1 | 9/2019 | Black |
| 2019/0274718 A1 | 9/2019 | Denzinger et al. |
| 2019/0274750 A1 | 9/2019 | Jayme et al. |
| 2019/0274752 A1 | 9/2019 | Denzinger et al. |
| 2019/0321066 A1 | 10/2019 | Voic et al. |
| 2020/0078609 A1 | 3/2020 | Messerly et al. |
| 2021/0059706 A1 | 3/2021 | Downey et al. |

FOREIGN PATENT DOCUMENTS

| | | |
|---|---|---|
| CN | 103027748 A | 4/2013 |
| EP | 1199047 A2 | 4/2002 |
| EP | 1518505 A1 | 3/2005 |
| EP | 2578172 A2 | 4/2013 |
| JP | 2000140760 A | 5/2000 |
| JP | 2001500031 A | 1/2001 |
| JP | 2002078715 A | 3/2002 |
| JP | 2003093401 A | 4/2003 |
| JP | 2003153918 A | 5/2003 |
| JP | 2003305050 A | 10/2003 |
| JP | 2004000732 A | 1/2004 |
| JP | 2005066316 A | 3/2005 |
| JP | 2007090139 A | 4/2007 |
| JP | 2007530153 A | 11/2007 |
| JP | 2010500073 A | 1/2010 |
| KR | 20020081299 A | 10/2002 |
| KR | 20080003243 A | 1/2008 |
| KR | 20170039726 A | 4/2017 |
| WO | 2010146940 A1 | 12/2010 |
| WO | 2017149613 A1 | 9/2017 |
| WO | 2019173137 A1 | 9/2019 |
| WO | 2019173145 A1 | 9/2019 |
| WO | 2019173191 A1 | 9/2019 |
| WO | 2019173198 A1 | 9/2019 |
| WO | 2019173200 A1 | 9/2019 |
| WO | 2019204641 A1 | 10/2019 |

OTHER PUBLICATIONS

English language abstract and machine-assisted English translation for JP 2000-140760 extracted from espacenet.com database on Feb. 10, 2020, 30 pages.

English language abstract and machine-assisted English translation for JP 2002-078715 extracted from espacenet.com database on May 30, 2018, 19 pages.

English language abstract and machine-assisted English translation for JP 2004-000732 extracted from espacenet.com database on Feb. 10, 2020, 19 pages.

English language abstract and machine-assisted English translation for JP 2007-090139 extracted from espacenet.com database on May 30, 2018, 38 pages.

English language abstract for CN 103027748 extracted from espacenet.com database on Nov. 13, 2017, 2 pages.

English language abstract for JP 2001-500031 A extracted from espacenet.com database on Jul. 19, 2022, 2 pages.

(56) References Cited

OTHER PUBLICATIONS

English language abstract for JP 2003-093401 A extracted from espacenet.com database on Dec. 13, 2021, 1 page.
English language abstract for JP 2003-153918 A extracted from espacenet.com database on Jul. 19, 2022, 1 page.
English language abstract for JP 2003-305050 A extracted from espacenet.com database on Dec. 13, 2021, 2 pages.
English language abstract for JP 2005-066316 A extracted from espacenet.com database on Dec. 13, 2021, 2 pages.
English language abstract for JP 2010-500073 A extracted from espacenet.com database on Dec. 13, 2021, 2 pages.
English language abstract for KR 2002-0081299 A exttracted from espacenet.com database on Jul. 19, 2022, 1 page.
English language abstract for KR 2008-0003243 A extracted from espacenet.com database on Jul. 19, 2022, 2 pages.
English language abstract for WO 2017/149613 extracted from espacenet.com database on Dec. 22, 2020, 1 page.
International Search Report for Application No. PCT/US2014/050034 dated Dec. 2, 2014, 5 pages.
Vankka, Jouko, "Direct Digital Synthesizers: Theory, Design and Applications", Helsinki University of Technology, Nov. 2000, 208 pages.
English language abstract for JP 2007-530153 A extracted from espacenet.com database on May 14, 2024, 2 pages.
English language abstract for WO 2010/146940 A1 extracted from espacenet.com database on May 14, 2024, 2 pages.

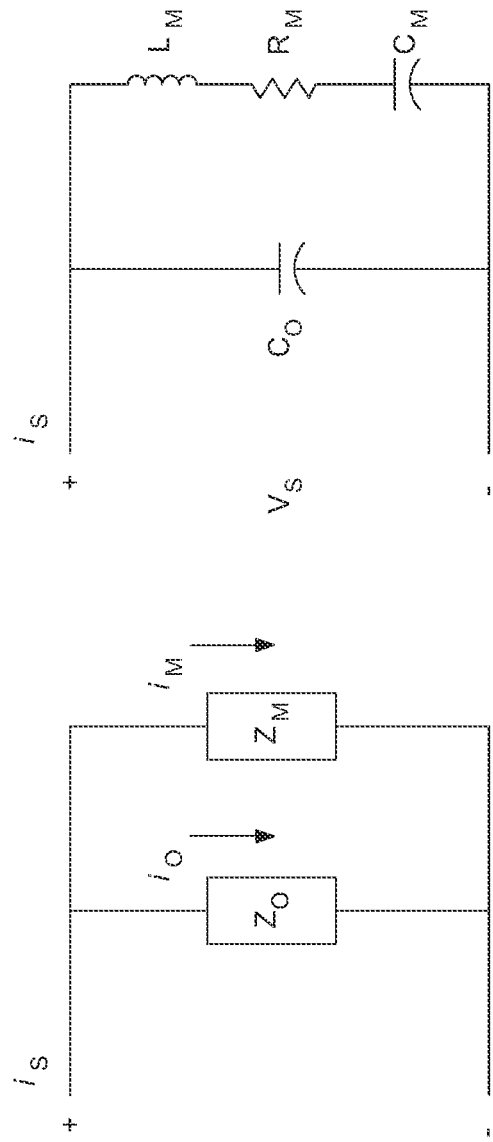
FIG. 4B
FIG. 4A
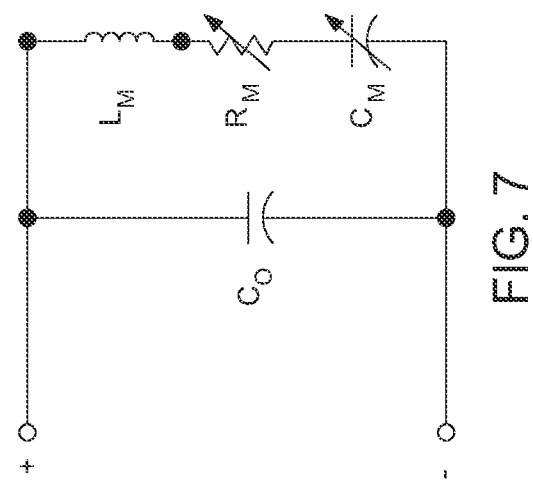
FIG. 7

| | |
|---|---|
| TIP ID DATA | 218 |
| CURRENT $i_S^{MAX}$ | 220 |
| CURRENT $i_M^{MAX}$ | 222 |
| VOLTAGE $v_S^{MAX}$ | 224 |
| MIN DRIVE FREQ. | 226 |
| MAX DRIVE FREQ. | 228 |
| PID COEFFICIENTS | 230 |
| TIP USE HISTORY | 232 |
| TARGET FREQUENCY | 234 |
| VIRT. IMPED. COEF. | 236 |

SYSTEM AND METHOD FOR DRIVING AN ULTRASONIC HANDPIECE AS A FUNCTION OF THE MECHANICAL IMPEDANCE OF THE HANDPIECE

CROSS-REFERENCE TO RELATED APPLICATIONS

This application is a continuation of U.S. patent application Ser. No. 17/096,293, filed Nov. 12, 2020, which is a continuation of U.S. patent application Ser. No. 15/981,986, filed May 17, 2018, which is a continuation of U.S. patent application Ser. No. 15/014,412, filed Feb. 3, 2016, which is a continuation of PCT Patent Application No. PCT/US2014/050034, filed Aug. 7, 2014, which claims the benefit of U.S. Provisional Patent Application No. 61/863,152, filed Aug. 7, 2013. The advantages and disclosures of each of these applications are hereby incorporated by reference herein in their entirety.

FIELD

This disclosure relates generally to an ultrasonically driven surgical handpiece. More particularly, this disclosure relates to applying a drive signal to the handpiece as a function of the changes of the impedance of the mechanical components of the handpiece.

BACKGROUND

Ultrasonic surgical instruments are useful surgical instruments for performing certain medical and surgical procedures. Generally, an ultrasonic surgical tool includes a handpiece that contains at least one piezoelectric driver. A tip is mechanically coupled to the driver and extends forward from the housing or shell in which the driver is disposed. The tip has a head. The head is provided with features, often teeth or flutes dimensioned to accomplish a specific medical/surgical task. An ultrasonic tool system also includes a control console. The control console supplies an AC drive signal to the driver. Upon the application of the drive signal to the driver, the driver cyclically expands and contracts. The expansion/contraction of the driver induces a like movement in the tip and, more particularly, the head of the tip. When the tip so moves, the tip is considered to be vibrating. The vibrating head of the tip is applied against tissue in order to perform a specific surgical or medical task. For example, some tip heads are applied against hard tissue. One form of hard tissue is bone. When this type of tip head is vibrated, the back and forth vibrations of the tip head remove, saw the adjacent hard tissue. Still other tip heads are designed to be placed against soft tissue. When this tip head vibrates the teeth often remove the tissue by a cutting action. Some ultrasonic tools also remove tissue by inducing cavitation in the tissue and surrounding fluid. Cavitation occurs as a result of the tip head moving back and forth. Specifically, as a result of these vibrations, small voids, cavities, form in the tissue and surrounding fluid. These cavities are very small zones of extremely low pressure. A pressure differential develops between contents of the cells forming the tissue and these cavities. Owing to the relatively large magnitude of this pressure differential, the cell walls burst. The bursting of these cell walls, removes, ablates, the cells forming the tissue.

The head of an ultrasonic tip is often relatively small. Some heads have diameters of less than 1.0 cm. An ultrasonic tool essentially only removes the tissue adjacent to where the head is applied. Thus owing to the relative small surface area of their heads, ultrasonic handpieces have proven to be useful tools for precisely removing both hard and soft tissue.

For an ultrasonic surgical instrument, sometimes called a handpiece or a tool, to efficiently function, a drive signal having the appropriate characteristics should be applied to the tool. If the drive signal does not have the appropriate characteristics, the tip head may undergo vibrations of less than optimal amplitude and/or may not vibrate as fast as possible. If the handpiece is in either state, the ability of the handpiece to, at a given instant, remove tissue may be appreciably reduced.

One means of ensuring an ultrasonic handpiece operates efficiently is to apply a drive signal to the handpiece that is at the resonant frequency of the handpiece. When the drive signal is at given voltage or current, the application of the drive signal at the resonant frequency induces vibrations in the tip that are at a relatively large amplitude in comparison to the application of the same voltage at a frequency that is off resonance.

Still other ultrasonic tool systems are designed to apply a drive signal at the anti-resonant frequency of the handpiece. The anti-resonant frequency may be a frequency at which the handpiece would have the highest impedance.

Applicant's SONOPET® Ultrasonic Aspirator includes a console with components designed to generate and apply a variable drive signal to the attached handpiece. Internal to the console is a resonance circuit. At the time of manufacture of the console, the inductance and capacitance of this resonance circuit are set as a function based on the impedance of the specific handpiece with which the console is intended to be used. The characteristics of the drive signal output by the console is set as a function of the voltage across this impedance circuit.

For many procedures, the SONOPET Console outputs a drive signal that at least is close to if not essentially identical to the resonant frequency of the mechanical components of the handpiece. However, in many normal use situations, an ultrasonic handpiece may be subjected to a significant mechanical load. This can happen, for example, when the tip is pressed against bone. In this situation, the mechanical load placed on the tip may cause a significant change in the impedance of the mechanical components of the handpiece. If this event occurs, the control console may not be able to output a drive signal at a frequency near the resonant frequency of the mechanical components of the handpiece.

Further, the impedance circuit internal to prior art console typically has an inductance and a capacitance that are set as a function of the specific handpiece with which the console is to be used. If a handpiece with different internal inductances, capacitances and resistances is attached to the console, there is an appreciable likelihood that the drive signal output by the console will not have the characteristics that facilitate the efficient operation of the handpiece. This makes it difficult, if not impossible, to use a console designed for use with one handpiece as the power supply to source a drive signal to another handpiece.

SUMMARY

This disclosure is directed to a new and useful ultrasonic surgical tool system. The tool system of this disclosure is designed to ensure that, within design limits, the drive signal applied to the system handpiece induces vibrations of appropriate amplitude in the handpiece tip. More particularly, the system is able to so set the drive signal when different handpieces are attached to the control console. The system also adjusts the characteristics of the drive signal when, as a consequence of the use of the handpiece, the impedance characteristics of the handpiece changes.

The system of this disclosure includes a control console to which a handpiece is attached. The control console generates and sources the drive signal to the handpiece. The control console sets the frequency of the drive signal and the current sourced to the handpiece. The current sourced is set by regulating the voltage of the drive signal. These characteristics of the drive signal are set as function of two variables and a constant. One of the variables is the voltage of the drive signal. The second variable is the current through the handpiece, the current of the drive signal. The constant, is the capacitance of the one or more piezoelectric drivers internal to the handpiece.

Based on these three inputs, the control console sets the frequency and voltage level of the drive signal. The frequency of the drive signal is set to, as closely as possible, match a target frequency. This is to ensure that vibrations of the tip head are at their most efficient frequency. The voltage is set to provide control over the amplitude of the tip head vibrations.

In some versions of the disclosure, the drive signal is adjusted to regulate the equivalent of current applied to the mechanical components of the handpiece. The frequency of the drive signal may be adjusted to ensure that the signal is at a target frequency related to resonance and/or anti-resonance frequency of the mechanical components of the handpiece.

The voltage and current of the drive signal are measured by circuits internal to the control console.

The driver capacitance is considered a constant in that for many successive adjustment of the drive signal, this capacitance remains unchanged. In some versions of the disclosure driver capacitance is obtained from data read from a memory integral with the handpiece attached to the console. Alternatively, based on a set of interrogation signals, the console may periodically determine driver capacitance.

The target frequency of a handpiece is partially a function of the mechanical components of the handpiece. The target frequency is also a function of the changing load applied to these components. The target frequency can be the resonant frequency of the mechanical components of the handpiece. In some versions of the disclosure the target frequency is the anti-resonant frequency of the mechanical components of the handpiece. In still other versions of the disclosure, the target frequency is a frequency between the resonant and anti-resonant frequency of the mechanical components of the handpiece. In still other versions of the disclosure, the target frequency is outside of the band between the resonant and anti-resonant frequencies.

It is thus a feature of the system of this disclosure that the console selectively adjusts the drive signal. When the load applied to the handpiece results in a change in the target frequency, the drive signal is adjusted to remain at or near the target frequency.

An additional feature of this disclosure is that a console can source drive signals to handpiece with drivers having different capacitances. Likewise, there is no requirement that a handpiece of this disclosure only be connected to a single specific console.

In some alternative embodiments, only the frequency of the drive signal is set. This frequency is regulated to ensure that drive signal causes an equivalent of current applied to the mechanical components of the handpiece and that the signal be at a frequency close to a desired target frequency for these components.

BRIEF DESCRIPTION OF THE DRAWINGS

The invention is pointed out with particularity in the claims. The above and further features and benefits of this disclosure are understood from the following Detailed Description taken in conjunction with the following drawings in which:

FIGS. 4A and 4B are representations of current flow through the handpiece and the impedances of the different components of the handpiece

FIG. 7 depicts how the impedance circuit formed by the components internal to the handpiece can be considered to change form when the handpiece is subjected to a mechanical load;

FIG. 13 depicts types of data stored in the memory internal to the tip;

DETAILED DESCRIPTION

I. System Overview and Hardware

Figure 1:
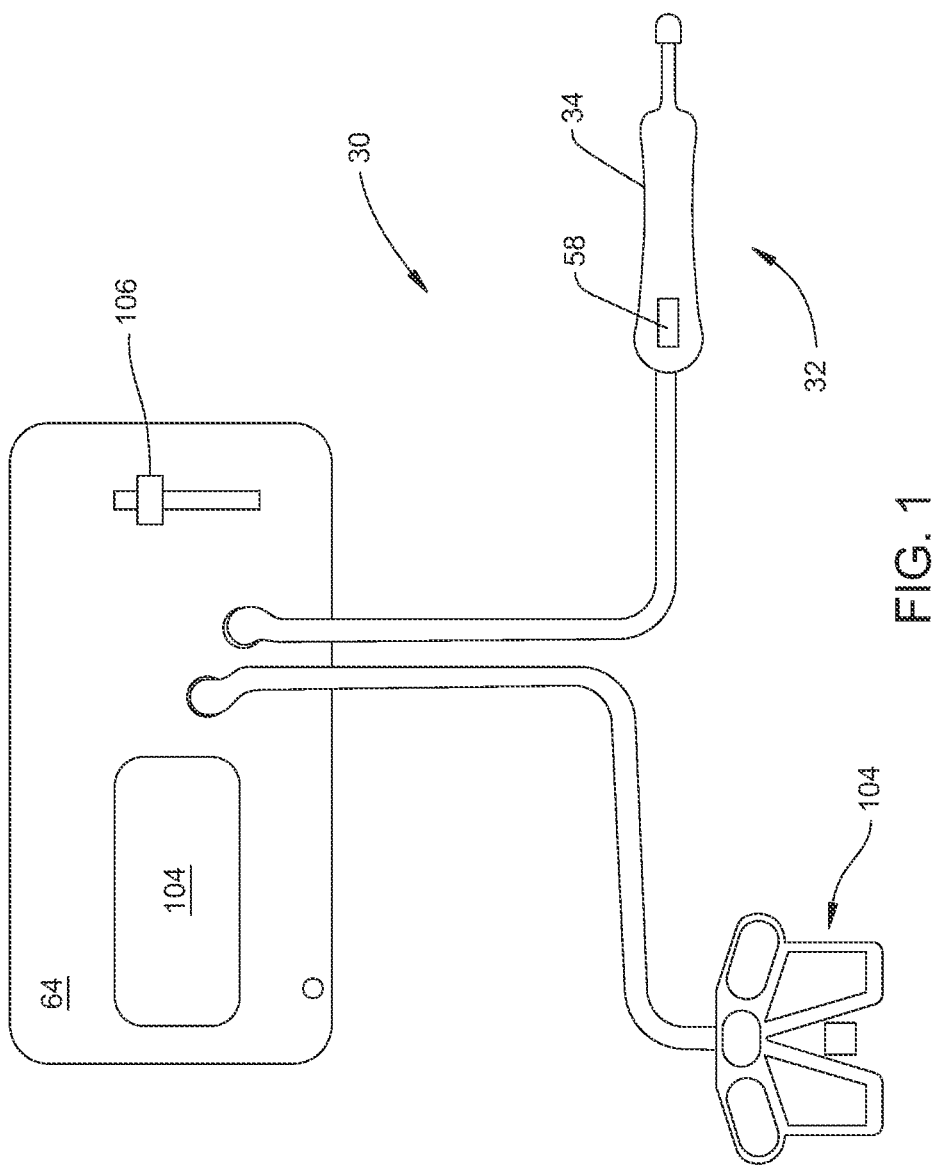
FIG. 1 depicts the basic components of an ultrasonic tool system that includes the features of this disclosure.

An ultrasonic tool system 30 is now generally described by reference to FIGS. 1 and 2. System 30 includes a handpiece 32. Handpiece 32 includes a body or shell 34 that forms the proximal end of the handpiece. ("Proximal" is understood to mean towards the practitioner holding the handpiece, away from the site to which the handpiece is applied. "Distal" is understood to mean away from the practitioner, towards the site to which the handpiece is applied.)

One or more vibrating piezoelectric drivers 40 (four shown) are disposed inside shell 34. Each driver 40 is formed from material that, when a current is applied to the driver, undergoes a momentary expansion or contraction. These expansions/contractions are on the longitudinal axis of a driver 40, the axis that extends between the proximally and distally directed faces of the driver. A pair of leads 41 extends away from each driver 40. The leads 41 are attached to the opposed proximally and distally directed faces of the drivers. Many, but not all handpieces 32, include piezoelectric drivers 40 that are disc shaped. These drivers 40 are arranged end to end in a stack. Leads 41 are the components of system 30 which the current, in the form of a drive signal, is applied to the drivers 40. Insulating discs 37, one shown, separate adjacent leads 41 connected to adjacent drivers 40 from each other. In FIG. 2, drivers 40 are shown spaced apart from each other. This is for ease of illustrating the components. In practice insulating discs 37 and drivers 40 tightly abut.

A post 39 extends longitudinally through insulating discs 37 and the drivers 40. The post 39 extends through the drivers along the collinear longitudinal axes of the drivers. Not seen are through bores internal to the insulating discs 37 and drivers 40 and through which the post 39 extends. Post 39 projects outwardly of both the most proximally located driver 40 and the most distally located driver.

A proximal end mass 36 is attached to the proximally directed face of the most proximally located driver 40. The exposed proximal end section of the post 39 is fixedly attached to mass 36. If post 39 is threaded, then mass 36 may be a nut.

A horn 42 extends forward from the distally directed face of the most distally located driver 40. While not shown, an insulating disc 37 may be present between these components. Horn 42 has a base with a diameter approximately equal to the diameter of the drivers 40. Extending distally forward from the drivers, the diameter of the horn 42 decreases. The exposed distal end section of post 39 is affixed to the horn 42. If the post 39 is threaded, the horn base may be formed with a threaded closed end bore (not identified) for receiving the post 39. Handpiece 32 is constructed so that the stack of drivers 40 is compressed between proximal mass 36 and horn 42.

A tip 48 extends forward from the distal end of the horn 42. A coupling assembly, represented by a collar 44, typically removably holds the tip 48 to horn 42 and the rest of the handpiece 32. The structure of the coupling assembly is not part of the present disclosure. Tip 48 includes an elongated stem 50. Stem 50 is the portion of the tip that, through the coupling assembly, is attached to the horn 42. Stem 50 extends forward of the handpiece shell 34. Tip 48 is formed so as to have a head 52 at the distal end of stem 50. Some tip heads 52 have smooth surfaces. Some heads 52 are formed with teeth 53. The geometry of the head 52 is not part of the present disclosure. Tip head 52 is the portion of the handpiece 32 applied to the site on the patient at which the procedure is performed.

Some tips 48 are provided with teeth designed to be applied directly to hard tissue, bone. When this type of type is reciprocated, the teeth cut the tissue in the same manner in which a conventional saw blade cuts tissue.

Figure 2:
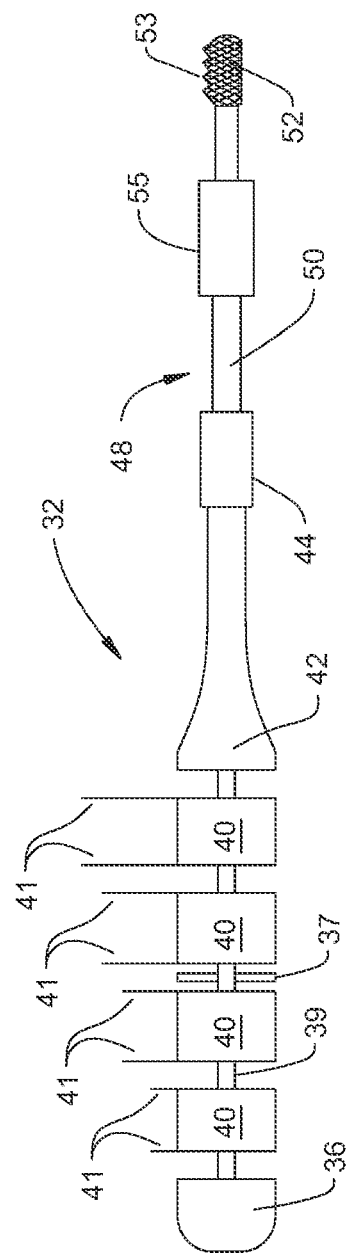
FIG. 2 is a diagrammatic depiction of the mechanical components of the tool, the handpiece of the system.

A sleeve 55, depicted as a ring in FIG. 2, is typically disposed over tip stem 50. Sleeve 55 typically extends from a location near where the stem is attached to the horn 42 to a location approximately 0.5 cm proximal to the head 52. Collectively the handpiece 32, tip 48 and sleeve 55 are constructed so that the sleeve defines a fluid flow conduit that extends between the outer surface of the tip and the surrounding inner surface of the sleeve. The sleeve 55 also has a fitting (not seen) adjacent the proximal end of the sleeve that extends to this conduit. The conduit is open at the distal end of the sleeve. When the handpiece is in use an irrigating solution is flowed from the sleeve fitting, down the sleeve and discharged adjacent the tip head 52. In some versions of the system the fluid serves as a medium through which the mechanical vibrations of the tip head are transferred to the tissue. This irrigating solution also functions as a heat sink for the thermal energy developed by the tip head as a consequence of the vibration of the head.

While not seen, the tip, the horn 42 and handpiece post 39 are often formed with conduits that collectively define a fluid flow path from the tip head 52 to the proximal end of the handpiece. When the handpiece is in operation, suction is drawn through these conduits. The suction draws the irrigating fluid discharged through the sleeve 55 away from the site to which the tip is applied. The suction also draws the tissue towards the tip head. The shortening of the distance between the tip head and the tissue improves the transmission of the mechanical vibrations from the tip head to the tissue.

Handpiece 32 also includes a memory 58. Memory 58, as discussed below, contains data describing the characteristics of the handpiece. Memory 58 may take the form of an EPROM, an EEPROM or an RFID tag. The structure of the memory is not part of the disclosure. Most handpieces 32 of this disclosure include a memory that, in addition to containing data capable of being read are able to store data written to the memory after manufacture of the handpiece. Ancillary components not illustrated are mounted to the handpiece to facilitate the reading of data from and the writing of data to the memory. These components consist of one or more of the following: conductors; exposed contacts/contact pins; a coil/antenna; or an isolation circuit.

A control console 64 is also part of system 30 of this disclosure. Control console 64 sources drive signals over a cable 62 to which handpiece 32 is connected. In many but not all versions of system 30, handpiece 32 and cable 62 are assembled as a single unit. The drive signals are applied to the drivers 40. At any given instant, the same drive signal is applied to each driver 40. The application of the drive signals causes the drivers to simultaneously and cyclically expand and contract. A stack of drivers 40 is often between 1 and 5 cm in length. The distance, the amplitude, of movement over a single expansion/contraction cycle of the drivers may be between 1 and 10 microns. Horn 42 amplifies this movement. Consequently the distal end of the horn 42 and, by extension, tip head 52 when moving from the fully contracted position to the fully extended position moves typically a maximum of 1000 microns and more often 500 microns or less. Some tips 48 are further designed to so that the longitudinal extension/retraction of the tip stem also induces a rotational movement in the head. When handpiece 32 is actuated to cause the cyclic movement of the tip, the head 52 is considered to be vibrating.

Figure 3:
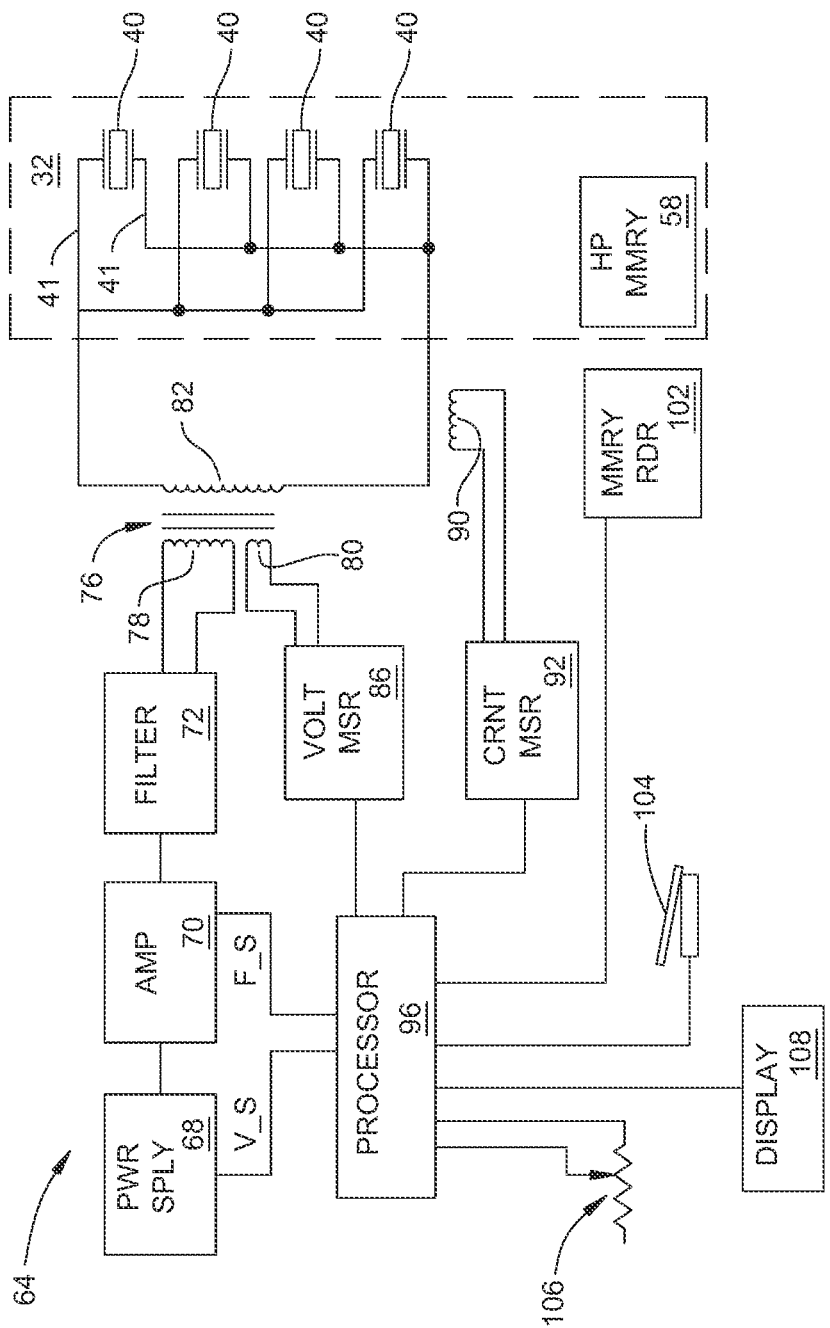
FIG. 3 is a block diagram of the electrical components of both the control console and handpiece components of the system of this disclosure.

The components internal to control console 64, as seen in FIG. 3, include a power supply 68. Power supply 68 outputs a constant voltage signal typically between 1 and 250 VDC. In many versions of the disclosure, the maximum potential of the voltage output by power supply 68 is 150 VDC or less. The potential of the signal output by power supply 68 can be selectively set. In described version of the disclosure, power supply 68 receives a VOLTAGE_SET (V_S) signal. Power supply 68 establishes the level of the output voltage as a function the VOLTAGE_SET signal. The output voltage produced by power supply 68 is applied to an adjustable amplifier 70. A control signal, specifically a FREQUENCY_SET (F_S) signal, is applied to amplifier 70. The frequency of the output signal produced by amplifier 70 is a function of the FREQUENCY_SET signal. The output signal from the amplifier 70 is applied to a filter 72. In some versions of the disclosure amplifier 70 is often a Class-D amplifier. The output signal from the amplifier 70 is applied to a filter 72. Filter 72 outputs a sinusoidal version of the square wave applied to the filter from amplifier 70. In some versions of the disclosure, filter 72 is a band pass filter. The signal output from filter 72 is typically between 10 kHz and 100 kHz. Often the signal has a minimum frequency of 20 kHz.

The output signal from filter 72 is applied to the primary winding 78 of a transformer 76, also part of the control console 64. The voltage present across the secondary winding 82 of the transformer 76 is the drive signal applied through cable 62 to the handpiece drivers 40. This voltage is typically a maximum of 1500 volts AC peak. The drive signal is applied in parallel across the drivers 40. More particularly, the drive signal is applied in parallel across each pair of leads 41.

Transformer 76 includes a tickler coil 80. The voltage present across tickler coil 80 is applied to a voltage measuring circuit 86. Based on the signal across tickler coil 80, circuit 86 produces a signal representative of the potential and phase of voltage $V_S$, the voltage of the drive signal applied to the handpiece 32. A coil 90, also disposed in control console 64, is located in close proximity to one of the conductors that extends from the transformer secondary winding 82. The signal across coil 90 is applied to a current measuring circuit 92. Circuit 92 produces a signal representative of the magnitude and phase of current $i_S$, the current of the drive signal sourced to the handpiece.

The $V_S$ and $i_S$ signals representative of the characteristics of the drive signal sourced to the piezoelectric driver 40 are applied to a processor 96 also internal to the control console 64. Control console 64 also includes a memory reader 102. Memory reader 102 is capable of reading the data in handpiece memory 58. The structure of memory reader 102 complements the handpiece memory 102. Thus, memory reader can be: an assembly capable of reading data in a EPROM or EEPROM or an assembly capable of interrogating and reading data from an RFID tag. In versions of the disclosure in which the data read from the memory 58 are read over the conductors over which the drive signal is sourced to the handpiece 32, the memory reader may include an isolation circuit. Data read by reader 102 are applied to processor 96.

Processor 96 generates the VOLTAGE_SET signal applied to power supply 68. The processor 96 also generates the FREQUENCY_SET signal applied to amplifier 70. These are the control signals that regulate the voltage and frequency of the drive signal sourced by the control console 64. Processor 96 asserts the control signals as a function of the characteristics of the handpiece and acquired measurements of $V_s$ and $i_s$.

Connected to control console 64 is an on/off switch. In FIG. 1, the on/off switch is represented by a foot pedal 104. The state of pedal 104 is monitored by processor 96. The on/off switch is the user actuated control member that regulates the on/off state of the system 30. In FIG. 1, foot pedal 104 is shown as being part of a foot pedal assembly that includes plural pedals. The added pedals may be used to control devices such as irrigation pump, a suction pump or a light. These supplemental devices are not part of the current disclosure.

Control console 64 is shown as having a slide switch 106. Like switch 104, the state of switch 106 is monitored by processor 96. Switch 106 is set by the practitioner to control the magnitude of the amplitude of the vibrations of tip head 52. Foot pedal 104 and switch 106 are understood to be general representations of the means of enter on/off and amplitude setting commands to system 30. In some constructions of the system a single control member may perform both functions. Thus the system may be configured so that when a lever or foot pedal is initially first depressed, the system causes tip head to undergo a vibration cycle that is of relatively small amplitude. As a result of the continued depression of the lever or foot pedal, the control console resets the drive signal applied to the handpiece so as to cause tip head 52 to undergo vibration cycles that are of a larger magnitude.

A display 108 is built into control console 64. The image on display 108 is shown as being generated by processor 96. Information depicted on display 108 includes information identifying the handpiece and possibly the tip; information describing characteristics of the operating rate of the system.

II. Fundamentals of Operation

The components forming the control console 64 are collectively configured to output a drive signal to the handpiece that, ideally, results in relatively large back and forth reciprocal vibrations of the tip head 52. (The amplitude of head movement is as large as possible.) This is because the effectiveness of the ability of the tip to remove tissue is generally related to the length of movement of the tip head against the tissue.

One means to foster large amplitude reciprocation of the tip head 52 is to, within design limits, maximize and maintain the current of the drive signal applied to the handpiece. This is because there is a proportional relationship between the current applied to the handpiece 32 and amplitude of the movement of the tip head. The current $i_s$ applied to the handpiece can be mathematically considered to have two components depicted in FIGS. 4A and 4B: A first component is current $i_O$, the current applied to capacitance of the drivers 40. The second component is current $i_M$, a mathematical equivalent of current applied to the mechanical components of the handpiece 32. The mechanical components of the handpiece are the components of the handpiece that, in response to the application of the drive signal, vibrate. These components include: the proximal end mass 36; post 39; drivers 40; horn 42, including the coupling assembly; and the tip 48. Drivers 40 are included as part of these components because the drivers, since they vibrate, are part of the vibrating mechanical assembly of this disclosure. Sleeve 55 is typically not considered one of these components. This is because, while the sleeve 55 vibrates, the sleeve is not part of the vibrating system. More specifically, sleeve 55 can be considered a component that places a load on the vibrating system.

This system of this disclosure is designed to, independent in changes of the impedance of handpiece, hold the equivalent of current applied to the mechanical components, current $i_M$, constant.

Current $i_M$ is determined and, therefore, controlled, based on the impedance of the components forming handpiece 32. The drivers 40 and mechanical components of the handpiece can be considered to be two impedance circuits connected together in parallel. Here $Z_O$ is the impedance of the stack of drivers 40. Driver impedance is essentially a function of the capacitance $C_O$ of the drivers 40 and the frequency of the drive signal. This model assumes the capacitance of cable 62 and any other components over which the drive signal is applied to the drivers is negligible. Thus, impedance $Z_O$ only has a capacitive reactance component, $1/j\omega C_O$. Variable "$\omega$" is the radian frequency of the drive signal. Impedance $Z_O$ has a negligible resistive and inductive reactance components.

Impedance $Z_M$ is the mathematical equivalent of the effective impedance of the mechanical components of the handpiece. Impedance $Z_M$ is based on the mechanical equivalents of the inductance $L_M$, resistance $R_M$, and capacitance $C_M$. of the mechanical components of the handpiece. Impedance $Z_H$ is the overall impedance of the handpiece. Impedance $Z_H$ is therefore calculated according to the formula:

$$Z_H = \cfrac{1}{j\omega C_O + \cfrac{1}{j\omega L_M + R_M + \cfrac{1}{j\omega C_M}}} \quad (1)$$

For the model of FIGS. 4A and 4B:

$$i_s = i_O + i_M \quad (2)$$

Therefore:

$$i_M = i_s - i_O \quad (3)$$

Current through the drivers 40 is calculated according to the following formula:

$$i_O = \frac{V_S}{Z_O} \quad (4A)$$

$$= j\omega C_O V_S \quad (4B)$$

The above is based on the understanding that stack impedance is based solely on capacitance of the stack and frequency of the drive signal. Therefore, $$i_M = i_s - j\omega C_O V_S \quad (5)$$

In Equation (5) and the other Equations it should be understood that current $i_S$ and voltage $V_S$ are both vectors each of which having a magnitude component and a phase component. As discussed above, driver capacitance $C_O$ is known and, for the purposes of controlling the drive signal, constant. Assuming the frequency of the drive signal is relatively constant, one can then hold the drive current applied to the mechanical components of the handpiece constant by regulating $V_S$, the potential of the drive signal.

In addition to regulating the equivalent of current applied to the mechanical components of the handpiece 32, system 30 of this disclosure regulates the frequency of the drive signal. More particularly, the drive frequency is regulated so as to be at a target frequency based on the resonant frequency of the mechanical components of the handpiece 32. Often, but not always, the resonant frequency of the mechanical components is the target frequency. The resonant frequency is selected as the target frequency because, when the mechanical components vibrate at this frequency, assuming a constant equivalent of current, the handpiece cyclic expansions/contractions (vibrations) are at their highest amplitude. The particular type of resonance is referred to as mechanical resonance.

One process by which the frequency of the drive signal can be so set is based on the understanding that, at mechanical resonance, the current flows through the stack of drivers 40 and the mechanical components should be 90° out of phase. This is because, phase shifting effects of the capacitive reactance and the inductive reactance of the mechanical components of the handpiece cancel each other out. The drivers, at the frequency range at which the drive signal is applied, have a negligible inductive reactance. Consequently, the drivers induce a 90° phase shift in the current flow that is not induced in the equivalent of current that is applied to the mechanical components of the handpiece.

Currents $i_O$ and $i_M$ can be represented in polar form as $$i_O = A e^{j\Theta} \quad (6)$$

and $$i_M = B e^{j\Phi} \quad (7)$$

Constants A and B are proportional to the magnitude of the currents $i_O$ and $i_M$, respectively. Since the phase angle of the current through the mechanical components is 90° ($\Pi/2$ radians) out of phase with the current flow through the drivers:

$$\Phi = \Theta - \Pi/2 \quad (8)$$

The division of $i_O$ by $i_M$ leads to the following relationship:

$$\frac{i_O}{i_M} = \frac{A e^{j\Theta}}{B e^{j(\Theta-\Pi/2)}} = \frac{A}{B} e^{j\Pi/2} \quad (9A)$$

Converting the result of Equation (9A) into rectangular form leads to following result:

$$= \frac{A}{B}\cos(\pi/2) + j\frac{A}{B}\sin(\pi/2) \quad (9B)$$

$$= j\frac{A}{B}\sin(\pi/2) = j\frac{A}{B} \quad (9C)$$

The end result of Equation (9C) is based on the fact that the cosine of 90° is zero and the sine of 90° is one. This means that, when the handpiece is at mechanical resonance, the real component of the ratio of the current flow through the drivers 40 and the equivalent of current applied to the mechanical components of the handpiece is zero, mathematically:

$$-\text{Re}\left\{\frac{i_O}{i_M}\right\} = 0 \quad (10)$$

One reason the above ratio is negative is that it makes it possible to normalize the impedance of the handpiece from a resonance ratio–Re=0.0 to an anti-resonance ratio–Re=1.0. This facilitates ease of modeling the performance of the handpiece. Also, as discussed below assuming the ratio is negative simplifies the process associated with setting the frequency of the drive signal.

Substituting the driver current and equivalent of current applied to the mechanical components of the handpiece from Equations (4B) and (5) above into the relationship of Equation (10) means that, at mechanical resonance the following relationship holds true:

$$-\text{Re}\left\{\frac{j\omega V_S C_O}{i_S - j\omega V_S C_O}\right\} = 0 \quad (11)$$

Driver capacitance $C_O$ is constant. By injecting different frequencies into Equation (11) one can determine by an iterative process the frequency of the drive signal that matches the mechanical resonance of the handpiece. In regard to this process, it should be understood that, for a given potential and current, there is a linear relationship between frequency and the real component of the ratio of the current flow through the drivers 40 and the equivalent of current applied to the mechanical components of the handpiece. This means that by injecting two different frequencies into Equation (11) to determine ratio, it is possible to, by interpolation, determine the frequency that is relatively close to mechanical resonance.

III. Actual Operation

Figure 5:
FIG. 5 depicts types of data stored in the memory internal to the handpiece.

To facilitate operation of system 30, memory 58 internal to the handpiece is loaded with data during the assembly of the handpiece. These data, as represented by field 112 of FIG. 5, include data identifying the handpiece 32. These data are useful for verifying that the console 64 is able to apply a drive signal to the handpiece. Data in field 112 may also indicate the type of information regarding the handpiece that is presented on console display 108. Field 114 contains data indicating the capacitance $C_O$ of the stack of drivers 40. Driver capacitance can be determined by analysis during the process of assembling the handpiece 34. Often the sum of the capacitance of the drivers is between 500 to 5000 pF. Data regarding the maximum current that should be applied to the handpiece, current $i_S^{MAX}$, are contained in a field 116. Current $i_S^{MAX}$ is often less than 1 Amp peak and more often 0.5 Amp peak or smaller. Field 118 contains data indicating current $i_M^{MAX}$, the maximum equivalent of current that should be applied mechanical components of the handpiece. Current $i_M^{MAX}$ is typically 0.25 Amps peak or less. The maximum potential of the drive signal, voltage $V_S^{MAX}$, are stored in field 120. Voltage $V_S^{MAX}$ is often 1500 Volts AC peak.

Also stored in handpiece memory are data indicating the minimum and maximum frequencies of the drive signal that should be applied to handpiece 32. The minimum frequency, stored in field 122, is typically the minimum frequency of the drive signal that can be sourced by the control console. The maximum frequency of the drive signal, stored in field 124, is typically between 5 kHz and 40 kHz greater than the minimum frequency.

Field 126 contains coefficients for filtering the control signals output by controller 96. In many versions of the disclosure, the calculation of the VOLTAGE_SET and FREQUENCY_SET signals begins with the calculation of target values for these signals. PID control loops are used to establish the final levels for each of these signals. Field 126 contains the coefficients for each of these control loops. It should be understood that the data in fields 112, 116, 118, 120, 122, 124 and 126 like the data in field 114 are stored in the handpiece memory 58 as part of the process of assembling the handpiece.

Handpiece memory 58 also contains field 128 as a use history field. Control console 64, during use of the handpiece, writes data into field 128 so as to provide a log of the operation of the handpiece.

Figure 6A:
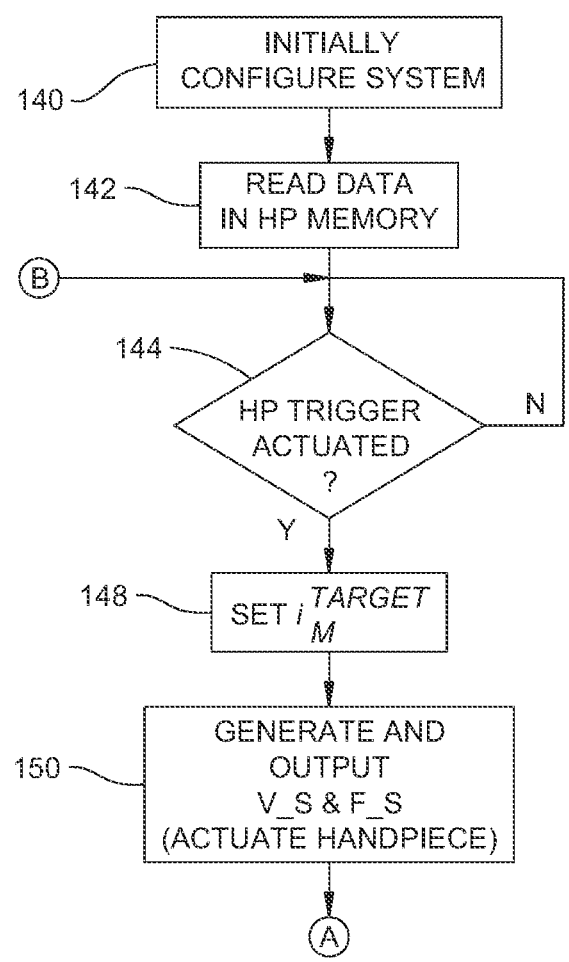
FIGS. 6A and 6B, when assembled together, form a flow chart of the operation of the system of this disclosure.
Figure 6B:
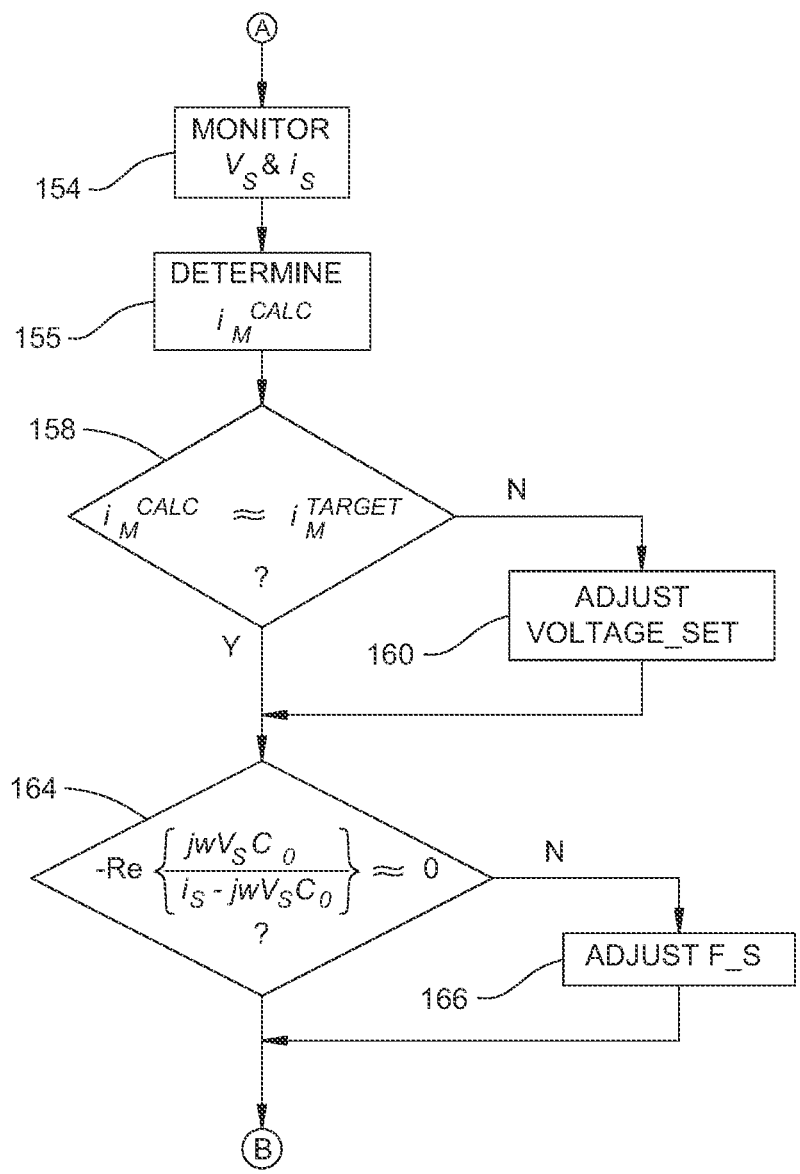

Operation of system 30 of this disclosure is understood by reference to the flow chart of FIGS. 6A and 6B. Step 140 represents the initial configuring of the system 30. Step 140 includes the attaching of the tip 48 to the handpiece 32. If cable 62 is not integral with handpiece 32, as part of step 140, the cable is connected to the handpiece 32. The cable 62 is connected to control console 64 to connect the handpiece to the console. If necessary, foot pedal 104 is attached to console 64. Prior to actuation of the handpiece the practitioner positions switch 106 to set the amplitude of the tip head vibrations.

Once the handpiece 34 is connected to the control console 64, in a step 142, console processor 96, through memory reader 102, reads the data stored in handpiece memory 58. Not shown and not part of the disclosure are any checks processor 96 may perform to verify that the console 64 can apply a drive signal to the handpiece 32. These checks are based on data stored in fields 112 and 128. These checks can include: verifying that the handpiece is one designed for use with the console; verifying that based on the use history, the handpiece is in condition to be actuated. Assuming the handpiece passes these checks, system 30 is ready for use.

Step 144 represents the processor 94 waiting for a signal from foot pedal 104 or other control member indicating that the practitioner wants to actuate the handpiece 32. Prior to the processor 96 receiving this signal, the processor does not assert the signals that result in the outputting a power signal from the power supply 68.

The practitioner actuates the handpiece by depressing the control member. Processor 96, in response to receiving a signal that this event has occurred, in a step 148, calculates a current $i_M^{TARGET}$ sometimes referred to as the target current. Target current $i_M^{TARGET}$ is the current that the processor determines should be applied to the mechanical components of the handpiece 32. Target current $i_M^{TARGET}$ is based on current $i_M^{MAX}$ retrieved from the handpiece memory and the practitioner's setting of the control 106 to adjust the amplitude of the tip vibrations. The target current can be calculated using a first order equation:

$$i_M^{TARGET} = D i_M^{MAX} \qquad (12)$$

Coefficient D is between 0.0 and 1.0, inclusive. If, for example, the practitioner sets the control to have the handpiece tip 50 undergo the vibrations of maximum amplitude, wants the handpiece tip to engage in vibrations having vibrations of the maximum amplitude, processor 64 sets coefficient D to unity. If the setting of control switch 106 indicates that the vibrations are to be at an amplitude less than the maximum, processor 64 sets coefficient D to a value less than one.

In a step 150, processor 96 then generates and outputs the VOLTAGE_SET signal. Initially the VOLTAGE_SET signal is set to cause the power supply to output a drive signal that is appreciably less than the maximum drive signal voltage $V_S^{MAX}$ retrieved from the handpiece memory 58. For example, in some versions of the disclosure this VOLTAGE_ SET signal is set to cause the drive signal to have an initial potential that is between 0.02 and 0.10 of voltage $V_S^{MAX}$. More particularly, the VOLTAGE_SET signal is set to have a potential that is between 0.03 and 0.07 of voltage $V_S^{MAX}$. The relationship between the voltage output by power supply 68 and voltage $V_S$ of the drive signal is typically a first order relationship. The determination of the VOLTAGE_SET signal as a function of the target drive signal voltage is based on potential of the target drive signal voltage and a coefficient and offset values previously stored in the processor 96.

As part of step 150, the FREQUENCY_SET signal is also generated and output by processor 96. When the control member is initially depressed to actuation the handpiece, processor 64 generates a FREQUENCY_SET signal that causes the console to output a drive signal at an initial frequency. This initial frequency can be the lowest possible frequency at which the drive signal should be applied to the handpiece; the highest possible frequency at which the drive signal should be applied; or any frequency between these two boundary frequencies.

While not specifically called out, in step 150 the processor asserts any necessary enable signals to the power supply 68, amplifier 70 and any safety components internal to the console. The assertion of these signals ensures that the power supply 68 outputs the necessary rail signal to the amplifier, the amplifier 70 outputs the intended square wave and the signal from which the drive signal is inductively obtained is applied to the transformer primary winding 78 of transfer 76.

As a result of the signal flow across transformer 76, the drive signal is applied to handpiece 32. This results in the cyclic expansion/contractions of the drivers 40. This movement of the drivers 40 vibrates tip head 52. Thus, the sub-steps that occur as a result of the execution of step 150 result in the actuation of the handpiece 34. Step 150 is continuously executed until, as discussed below, processor 96 determines that the practitioner wants to deactivate the handpiece 32.

System 30 then engages in a feedback control process to ensure that the output drive signal induces vibrations of appropriate amplitude in tip head 52. To perform this control, in step 154, the system monitors the system 96 monitors the voltage $V_S$ of the drive signal through the handpiece. This is the monitoring by processor 96 of the output signal produced by voltage measuring circuit 86. Also in step 154, the processor 96 monitors current is, the current through the handpiece. This is the monitoring of the output signal produced by current measuring circuit 92.

In a step 156, processor 96 determines the equivalent of current applied to the mechanical components of the handpiece, current $i_M^{CALC}$. Current $i_M^{CALC}$ is calculated based on Equation (5). Processor 96 is able to make this determination since it has data defining the four variables upon which this determination is based: current $i_S$ from the current measuring circuit 96; frequency ω based on the fact that processor sets the frequency of the drive signal; voltage $V_S$ from the voltage measuring circuit 86; and driver capacitance $C_o$. While driver capacitance $C_o$ is a variable in Equation (5) it is fixed and known variable read from the handpiece memory 58.

In a step 158 current $i_M^{CALC}$ is compared to current $i_M^{TARGET}$. More particularly, this comparison is made to determine if the actual current flow through the mechanical components of the handpiece is equal to or substantially the same as the target flow. Here, substantially the same is considered to be the state when the currents are within 20 or less mAmps of each other and more often 10 or less mAmps from each other. In some versions of system 30, if the equivalent of current applied to the mechanical components is below 50 mAmps, current $i_M^{CALC}$ is considered substantially same as current $i_M^{TARGET}$ if the difference in currents are 2 mAmps or less and, more typically, 1 mAmp or smaller. Alternatively, the currents can be considered substantially the same if they are within 10% or less of each other, more preferably within 5% or less of each and ideally, within 1% or less of each other.

If the currents are substantially equal, system 30 is in the state in which the equivalent of current applied to the mechanical components of the handpiece is at level at which the application of the drive signal assuming at the correct frequency, inducing vibrations of appropriate amplitude in tip head 52. If system 30 is in this state, processor 96 proceeds to step 164.

In many situations, the comparison of step 158 indicates that actual current $i_M^{CALC}$ is not substantially equal to target current $i_M^{TARGET}$. When system 30 is in this state, processor 96 in a step 160 resets the VOLTAGE_SET signal. More specifically, the processor 96 calculates a value for drive signal voltage $V_S$ that would, based on Equation (3), result in an adjusted current flow through the mechanical components of the handpiece that substantially equal to target current $i_M^{TARGET}$. This calculation of step 160 is executed based on driver capacitance and drive signal frequency remaining constant.

Then, in step 160, based on this new target value for drive signal potential, the VOLTAGE_SET signal is adjusted and output to power generator 68.

In step 164 the processor determines if the drive signal is at or substantially equal to the resonant frequency of the mechanical components of the handpiece. This determination is made by evaluating whether or not the ratio of Equation (11) is equal to or substantially equal to zero. Here, substantially equal to zero means Re is 0.10 or less, preferably 0.05 or less and more ideally 0.01 or less.

The comparison of step 164 may indicate that the drive signal applied to the handpiece is at or substantially equal to the resonant frequency of the mechanical components of the handpiece. This is the target state for the drive signal. This means that the drive signal is inducing expansions/contractions of the drivers 40 at a frequency that foster expansions/contractions to be of relatively high amplitude. By extension, this results in the tip head being actuated into vibrations of relatively high magnitude.

It may be determined in the evaluation of step 164 that the drive signal is not being applied to the handpiece at or near the resonant frequency of the mechanical components. If processor 96 makes this determination, in a step 166 the processor resets the frequency of the drive signal. Owing to the ratio on the left side of Equation (11) being negative, the calculation of step 164 yielding a negative result is, in step 166 interpreted as an indication by the processor 96 that the frequency of the drive signal should be increased. If the calculation of step 164 yields a positive result, processor 96 interprets the result as indicating the handpiece is in a state in which it is necessary to decrease the frequency of the drive signal in order to ensure that the drive frequency is closer to the resonant frequency of the mechanical components of the handpiece.

Processor 96 resets the frequency of the drive signal applied to the handpiece by adjusting the FREQUENCY_SET signal applied to amplifier 70. In step 166, processor assumes the current $i_S$, voltage $V_S$ and driver capacitance $C_O$ are constant. In the iterative process, different frequencies are injected into Equation (11). As a result of the new execution of Equation (11) it may be determined that the real components of the ratio of the current flow through the drives and the equivalent of current applied to the mechanical components of the handpiece is less (or substantially less) than zero. If this condition exists, then, in the next iteration the injected frequency will be greater than the previously injected frequency. As a result of the execution and evaluation of Equation (11) it may be determined that the ratio is greater (or substantially greater) than zero. If this condition exists, then, in the next iteration the injected frequency will be less than the previously injected frequency. If the end result of the calculation is that the ratio is zero or substantially zero, then the frequency of the drive signal is set to the injected frequency. Processor 166 then adjusts the FREQUENCY_SET signal output to amplifier 70 based on the results of this calculation. Control console 64 should then, in turn, output a drive signal to the handpiece that is at the resonant frequency of the mechanical components of the handpiece 32.

While not shown, it is understood that characteristics of the drive signal applied to the handpiece 32 are limited by the boundary parameters read from the handpiece. Specifically, the adjusting of the VOLTAGE_SET signal is limited to ensure that the drive signal does not exceed the potential specified by the maximum voltage level $V_S^{MAX}$. Adjustment of the VOLTAGE_SET signal is further limited to ensure the current of drive signal applied to the handpiece does not exceed $i_S^{MAX}$ and that the mechanical component of current does not exceed $i_M^{MAX}$.

In FIGS. 6A and 6B, after the execution of step 160 or, if necessary, step 164, the system is shown looping back to step 144. This is because the processes of recalculating target current $i_M^{TARGET}$ and selectively adjusting the potential and frequency of the drive signal are generally performed as long as the system remains actuated.

There are a number of reasons why the control loop is repetitively executed. Generally, it should be understood that, if as a result of the adjustment of the frequency of the drive signal is adjusted, there will be a change in the impedance of both driver impedance $Z_O$ and impedance $Z_M$ of the mechanical components of the handpiece. This results in a change of the current flow through the handpiece and, more particularly, the current $i_M^{CALC}$ through the mechanical components of the handpiece. System 30 detects these changes as changes in the measured values $V_S$ and $i_S$. Thus after step 164 is executed, the next evaluation of step 158 will most likely indicate that the system is in a state in which the current has shifted from the target current $i_M^{TARGET}$. This will necessitate a new execution of step 160 to adjust the magnitude of the voltage of the drive signal.

Similarly, the adjustment of the potential of the drive signal will also result in changes of voltage $V_S$ and current $i_S$. This means that the next time step 164 is executed the evaluation will indicate that the drive signal is no longer at the resonant frequency of the mechanical components of the handpiece.

After plural cyclings through the control loop, the console 64 asserts a drive signal that results in the current flow through the mechanical components of the handpiece that is substantially equal to $i_M^{TARGET}$ and is at the resonant frequency of the handpiece mechanical components. At start up, assuming the tip head is not applied against tissue, it is believed that the system reaches this state in 2 seconds or less and, more often 1 second or less.

A further reason the control loop is continuously executed has to do with very nature of how handpiece 32 is employed. For the handpiece to function, the head 52 is placed against tissue, (step not shown). This is because it is the back and forth movement of the teeth against the tissue that result in the sawing, the removal of, the tissue. Again, in some implementations of the disclosure, this back and forth movement is what results in the cavitation of the fluid adjacent the tissue and, in some instances the tissue itself.

When the head is placed against tissue, a mechanical load is placed on the components forming the handpiece. This mechanical load changes the impedance of the mechanical load of the handpiece. Also, when system 30 is actuated, the temperature of the mechanical components of the handpiece often change. This change in component temperature results in a change in the properties of these components. The change in component properties can cause a shift in the target frequency. These shifts in the characteristics of the mechanical components of the handpiece are depicted in FIG. 7 by the varying each of inductance $L_M$, resistance $R_M$ and capacitance $C_M$.

The resultant change in impedance and resonant frequency results in changes in the flow of both current $i_S$ through the handpiece and the current $i_M^{CALC}$ through the mechanical components. The continual execution of the control loop thus ensures that when these changes in impedance occur, the drive signal is reset to ensure that the mechanical component of the current is substantially equal to the target current $i_M^{TARGET}$ and the frequency of the drive signal is substantially equal to resonant frequency of the mechanical components of the handpiece. The maintaining of the characteristics of the drive signal close to these target parameters ensures that as the mechanical load to which the tip head 52 is exposed changes, the amplitude of the vibrations of the head remain substantially constant.

Further, during the time period in which the handpiece 32 is actuated, the practitioner may want to adjust the amplitude of tip head vibrations. This adjustment occurs by the resetting of switch 106 or similar control member. (Adjustment not illustrated.) Once this adjustment occurs, in the subsequent executions of step 148 the newly calculated target current $i_M^{TARGET}$ will be different than the previously calculated target current. This in turn will most likely mean that as a result of the next execution of step 158 it will be determined that the current $i_M^{CALC}$ is no longer substantially equal to the target current $i_M^{TARGET}$. For the reasons set forth above, this will most likely result in an adjusting of the potential and frequency of the drive signal.

Accordingly, the above described control loop starting with the evaluation of step 144 is continuously executed as long the foot pedal 104 or other on/off control remains actuated. The practitioner deactivates the handpiece by releasing the foot pedal 104. This results in the processor, in one of the subsequent executions of step 144, receiving a signal that this control member is in the off position. In response to processor 96 receiving this signal, the processor negates the application of the signals that were being asserted so as to cause the outputting of the drive signal, step not shown. System 30 returns to the wait state, the continuous monitoring of the signal from the on/off control member to determine if the practitioner wants to actuate the handpiece 32.

System 30 of this disclosure is constructed so that owing to the repetitive execution of steps 164 and 166, the system maintains the drive signal at a frequency that is substantially equal to the resonant frequency of the mechanical components of the handpiece 32. This relationship is maintained when the resonant frequency of the handpiece mechanical components changes due to the mechanical loading and/or temperature change of these components. Thus, the system disclosure is able to vibrate the head of the tip at the desired amplitude even when the tip and the other components of the handpiece are subjected to mechanical loading or undergo temperature changes. This reduces the need for the surgical personnel using the system having to continuously adjust the drive signal to ensure that the tip head continuously vibrates at the desired amplitude.

Also, during the course of a procedure the tip head may be suddenly pressed against tissue. This causes a rapid significant increase in the impedance of the mechanical components of the handpiece. In response to this rapid change in impedance, system 30 of this disclosure rapidly adjusts the potential and frequency of the drive signal. The adjustment of these characteristics of the drive signal serve to ensure that the tip head vibrations maintain the desired amplitude. This reduces the extent to which the sudden mechanical loading of the handpiece results in a like sudden reduction in the amplitude of the tip head vibrations.

A further feature of system 30 is that the system does not track to particular phase relationship between the voltage and current of the drive signal. Instead, system 30 tracks to the phase of the equivalent of the drive signal applied to the mechanical components of the handpiece. For the reasons discussed above, this ensures that the sourced drive signal has the characteristics that maintain the mechanical resonance of the handpiece.

System 30 of this disclosure is further configured so that control of the handpiece is not based on the matching of the capacitance, resistance or inductance of a component internal to the control console based to the characteristics of the handpiece. This means that a single console 64 can be used to construct a system 30 of this disclosure with different handpieces, each with its own driver capacitance. The console, based on the data read from the handpiece memory 58 describing the driver capacitance, configures the system for each handpiece. Likewise, a handpiece can be used with different control consoles to assembly the system 30 of this disclosure.

System 30 of this disclosure is further designed to apply an equivalent of current to the mechanical components of the handpiece that is substantially equal to the target current. This target current is based on the practitioner's setting of the desired amplitude of tip head vibrations. Thus, the system of this disclosure provides the practitioner with a relatively accurate means of controlling the amplitude of the tip head vibrations.

IV. First Alternative Method of Drive Signal Frequency Control

In an alternative construction of system 30 of this disclosure, the target frequency of the drive signal is set to the anti-resonant frequency of the mechanical components of the handpiece. The anti-resonant frequency is the frequency at which the impedance of the handpiece 32 is at a maximum. Ideally, this approaches infinity.

In this version of the disclosure, in step 164, the real component of the ratio of the current sourced to the piezoelectric drivers 40 and the equivalent of current applied to the mechanical components of the handpiece 32 is evaluated as follows $$-\mathrm{Re}\left\{\frac{j\omega V_S C_O}{i_S - j\omega V_S C_O}\right\} = 1 \qquad (13)$$

If the evaluation of step 164 does not result in a ratio substantially equal to 1, the processor injects different frequencies into Equation (13) in step 166. This process continues until the processor determines a frequency that is substantially equal to 1. This frequency is the anti-resonant frequency. The processor then outputs a FREQUENCY_SET signal that results in the control console sourcing a drive signal at this frequency.

In other versions of the disclosure, processor 96 may evaluate the real component of the ratio of the of the current sourced to the piezoelectric drivers 40 and the equivalent of current applied to the mechanical components of the handpiece 32 for a target frequency different than the resonant or anti-resonant frequency. Thus the evaluation may be to a value between 0 and 1 or even greater than 1.

V. Second and Third Alternative Methods of Drive Frequency Control

Figure 8:
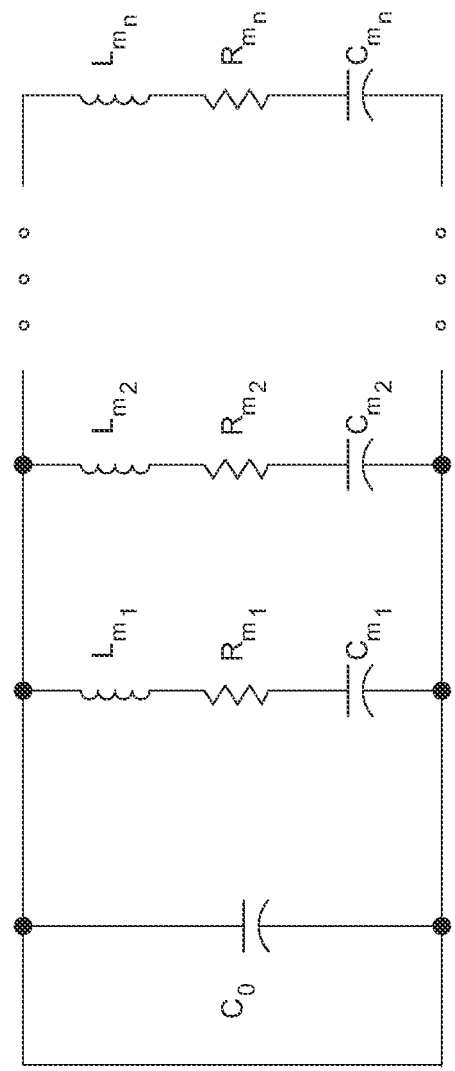
FIG. 8 represents an alternative model of the impedance of the handpiece drivers and the equivalent impedances of the mechanical components of the handpiece.

For some constructions of system 30 of this disclosure, the circuit of FIG. 4B is an overly simplified view of the impedance of the mechanical components forming the handpiece. For these versions of the disclosure, as represented by FIG. 8, mathematically, the mechanical components of some ultrasonic tools may be considered to comprise plural RLC series connected circuits that are connected together in parallel. This means that these components have, over a range of frequencies plural frequencies at which the components are in resonance; the reactive component of impedance is zero. The impedance $Z_H$ of this type of handpiece 32 and tip 48 is expressed as follows:

$$Z_H = \cfrac{1}{j\omega C_O + \cfrac{1}{j\omega L_{M_1} + R_{M_1} + \cfrac{1}{j\omega C_{M_1}}} + \cfrac{1}{j\omega L_{M_2} + R_{M_2} + \cfrac{1}{j\omega C_{M_2}}} + \cdots + \cfrac{1}{j\omega L_{M_n} + R_{M_n} + \cfrac{1}{j\omega C_{M_n}}}} \qquad (14)$$

Here $L_{M_1}$, $L_{M_2}$ ... $L_{M_n}$, $R_{M_1}$, $R_{M_2}$ .... $R_{M_n}$ and $C_{M_1}$, $C_{M_2}$ ... $C_{M_n}$ are, respectively the inductances, resistances and capacitances of each of the RLC branches of the mechanical components of the handpiece.

A difficulty applying a drive signal to this type of handpiece and tip assembly can arise if these plural resonant frequencies are within the range of frequencies over which the drive signal is to be applied to the handpiece. The nature of this problem is understood by reference to FIG. 9. Here, plot 182 represents the reactance over a range of frequencies for the mechanical components of the handpiece when the tip is operated in air. The drive signal is applied to the handpiece over a range of frequencies ranging from 25.20 to 25.65 kHz, the area within the two thick vertical lines 181 and 183 of FIG. 9. Within this frequency range, the reactive component of the mechanical impedance crosses the zero reactance point once, at approximately 25.54 kHz. The mechanical reactance of the handpiece also crosses the zero reactance point outside of the range of drive frequencies, at approximately 25.86 kHz. However, since second crossing is outside of the range at which control console 64 applies the drive signal, the fact that the mechanical reactance is zero at this frequency does not affect the operation of the system.

Plot 184 depicts the change in the reactance of the mechanical components of the handpiece over frequency when the tip, while vibrating, is pressed against a load. This load is understood to be the tissue the tip is intended to remove. As discussed above, this results in a change in the equivalent resistances and reactances of the mechanical components forming the handpiece. The reactance at a given frequency changes from plot 182 to plot 184. Here it is seen that within the range of frequencies at which the drive signal is applied the equivalent reactances of the mechanical components of the handpiece may cross the zero reactance point twice, at 25.30 kHz and 25.45 kHz.

For a particular handpiece and tip assembly to most efficiently function, it is typically desirable to apply a drive signal at frequency on or close to the lower of the two resonant frequencies. This lower of the two resonant frequencies is thus the target frequency. At a given instant when step 164 is executed, the results of the evaluation of step 164 may return a result that $$-\text{Re}\left\{\frac{j\omega V_S C_O}{i_S - j\omega C_S V_O}\right\} < 0$$

The above would be is the result would be returned when executing step 164 as described above if for the example of plot 184, the drive frequency is greater than 25.45 kHz.

If this is the result of the evaluation of step 164, in the execution of step 166 the control processor 66 increases the frequency of the drive signal. This results in the drive signal, actually drivers 40, vibrating the mechanical components of the handpiece at a frequency that is further away from the desired target frequency.

Figure 10:
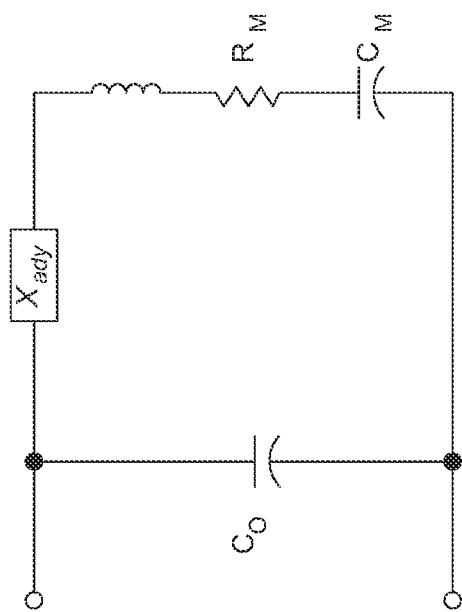
FIG. 10 is a schematic representation of the addition of a variable impedance to the mechanical components of the handpiece.

To reduce the likelihood of the above-identified event from occurring, in some versions of the disclosure, the system selectively adds a virtual impedance $X_{adj}$ to the impedance of the mechanical components of the handpiece. Schematically, as seen in FIG. 10 virtual impedance $X_{adj}$ is seen as being in series with the mathematical model of the impedance of the mechanical components of the handpiece.

Figure 9:
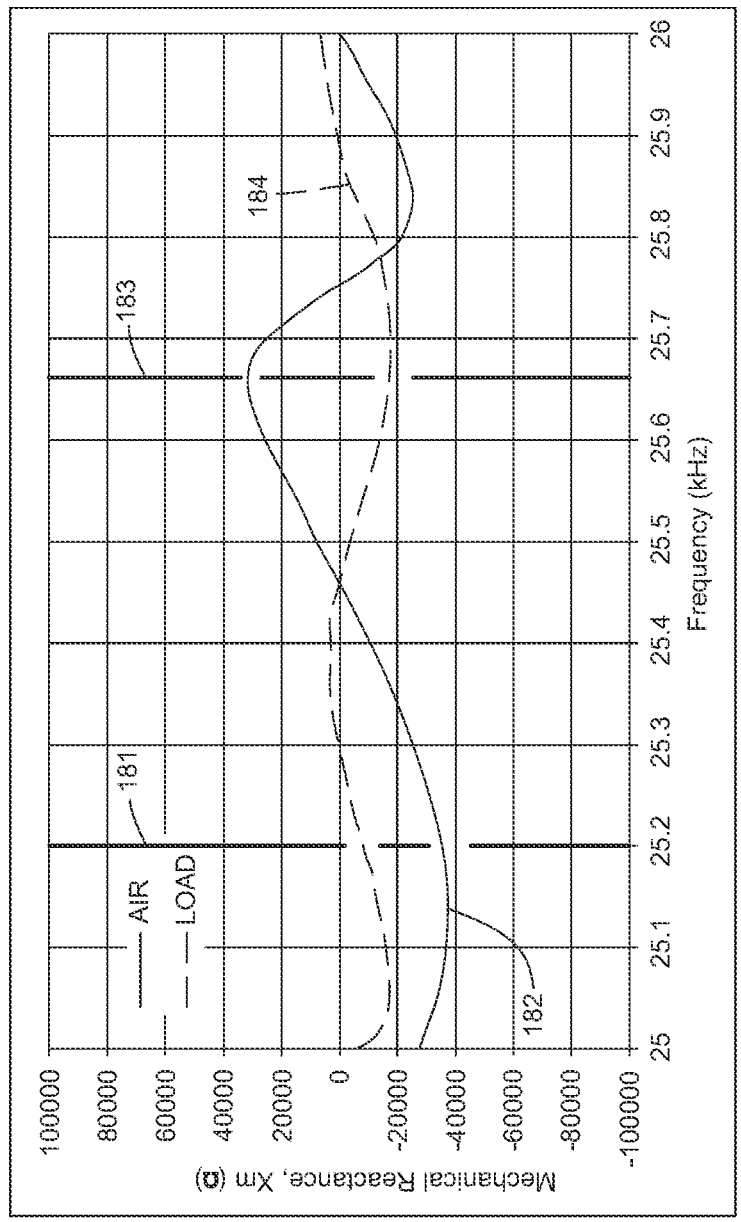
FIG. 9 is a graphical representation in the changes in the reactance of the mechanical reactance over frequency of the handpiece the tip is in air and when the tip is subjected to a load.
Figure 11:
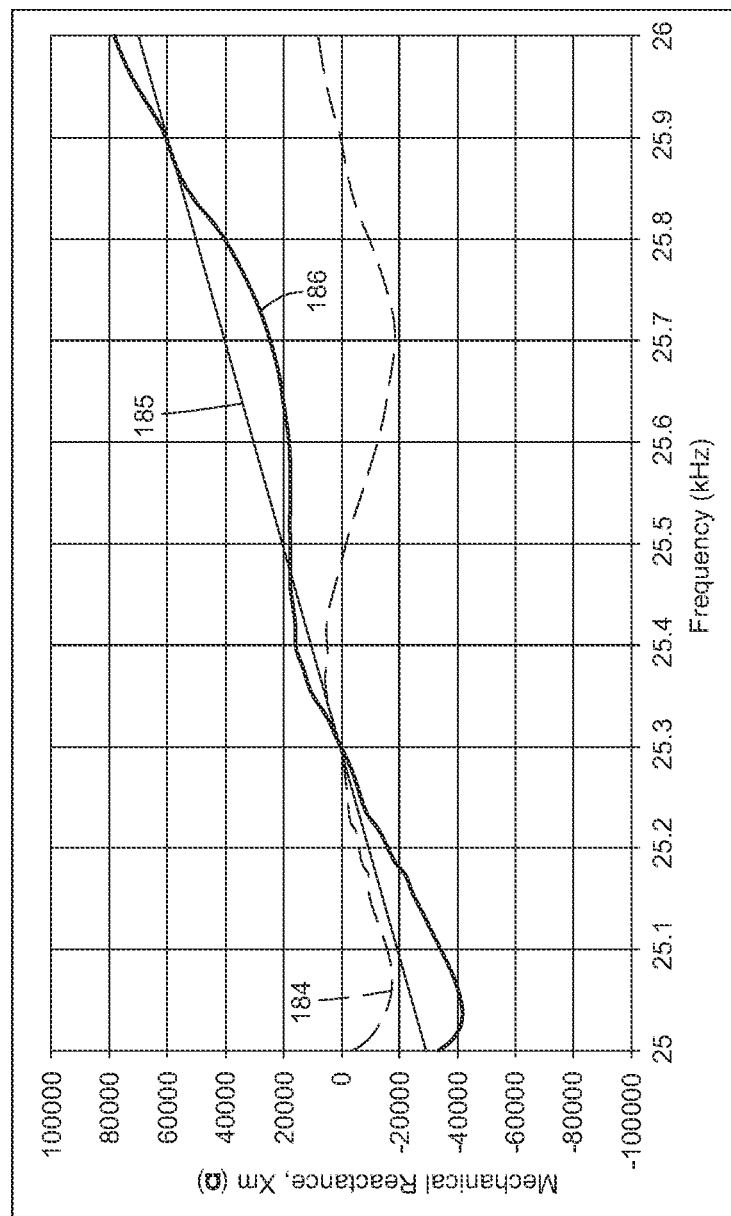
FIG. 11 is a graphical representation of how the addition of the variable impedance of the mechanical components of the handpiece effect the reactance of these components.

FIG. 11 depicts the effect of adding this virtual impedance to the impedance of the mechanical components of the handpiece. In FIG. 11, plot 184 is the same plot of reactance of the mechanical components of the handpiece when the tip is under load as seen in FIG. 9. Plot 185 is the reactive component of the virtual impedance $X_{adj}$. Here the reactive component of the virtual impedance is assumed to be zero at the frequency at which the reactance of the mechanical components of the handpiece is zero. Plot 186 is the sum of reactances of plots 184 and 186. As seen by plot 186 when the virtual reactance is added to the mechanical reactance, the total reactance has only a single zero crossing in the range of frequencies over which the drive frequencies are to be applied.

Figure 12:
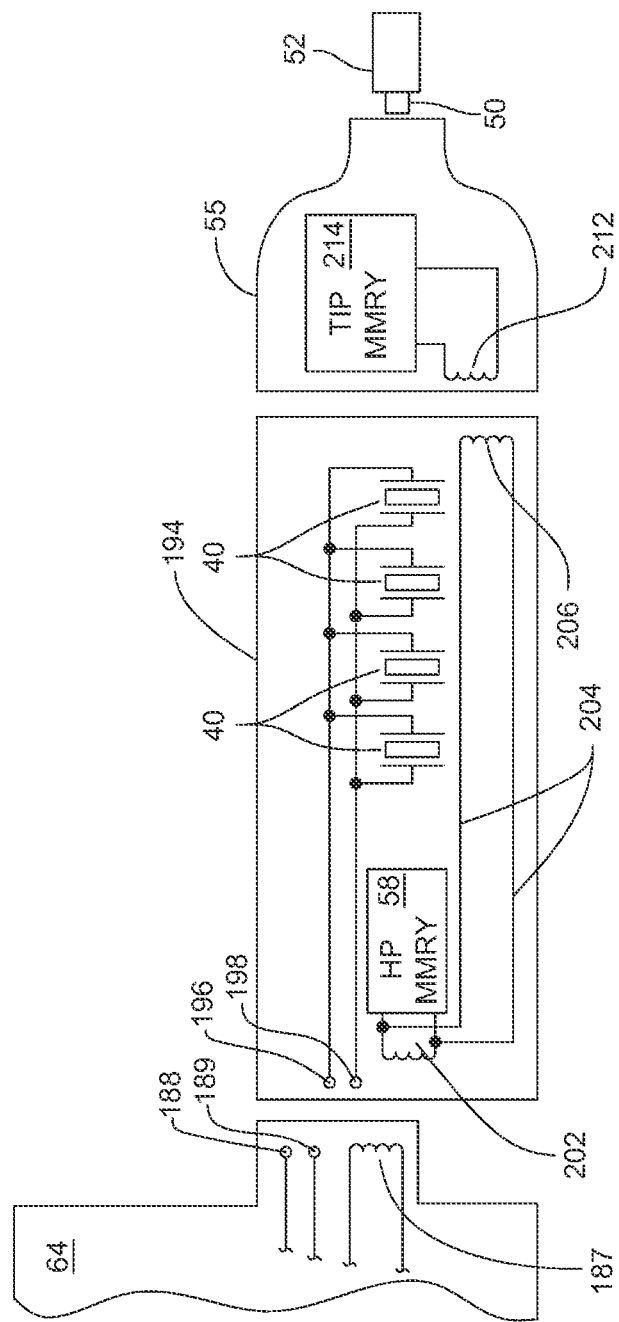
FIG. 12 is a block diagram depiction how data may be supplied from a memory integral with the tip of this disclosure to the control console.

FIG. 12 is a block and partial diagram of an alternative components of a version of this disclosure designed to add the virtual impedance into the real impedance of the mechanical components of the handpiece. Handpiece 190, depicted by rectangle, has the same features as previously described handpiece 32. These features include the conductive sockets or other contacts 196 and 198 to which the drive signal is sourced to drivers 40 internal to the handpiece. The drive signal is sourced from pins or other conductive contacts 188 and 189 integral with the control console socket to which the handpiece is connected. For ease of illustration, cable 62 is not seen in FIG. 12.

The specific memory 58 internal to handpiece 190 is an RFID tag. Since memory 58 is an RFID tag, also shown internal to handpiece 190 and connected to memory 58 is a coil or antenna 202. Coil 202 is understood to be in the end of the able connected to the control console socket. Coil 202 is configured and positioned to inductively exchange signals with a complementary coil 187 disposed in the console socket. While not shown, console coil 187 is connected to the console memory reader 102. Memory reader 102 converts the signals received over coil 187 into signals that can be read by processor 96. The memory reader 102 also outputs to the handpiece memory 58 the data processor 96 wants written to the memory.

A second coil, coil 206, is also disposed in the handpiece 190. While coil 202 is typically located adjacent the proximal end of the handpiece 190, coil 206 is typically located adjacent the distal end. More particularly, coil 206 is positioned to exchange signals with the below discussed sleeve coil 212. Conductors 204 internal to handpiece 190 connect coil 202 to coil 206.

Depicted as a tapered unit in FIG. 12 is the sleeve 55 from which tip 48 extends. Disposed within sleeve 55 is a tip memory 214. Memory 214 is referred to as the "tip memory" even though memory 214 is in sleeve 55 for two reasons. First, the tip 48 and sleeve 55 while separate components are typically packaged together as a kit. Secondly, the data contained in memory 55 is primarily used to control the actuation of the tip 48. Coil 212 which is embedded in sleeve 55 is connected to tip memory 55.

FIG. 13 depicts some of the data stored in the tip memory 214. A tip identification data field 218 contains tip identifying data analogues to the handpiece identifying data in field 112. There are minimum and maximum current fields 220 and 224. Field 220 and 222 contain data indicating the range of the equivalent of current that should be applied to the mechanical components of the handpiece for the specific tip with which memory 214 is associated. There is a maximum voltage field 224 similar to the maximum voltage field 120 in the handpiece memory. There are drive frequency fields 226 and 228. The data in fields 226 and 228 specify a tip specific range of frequencies for the drive signal that may be different from the frequency range of the handpiece drive signals specified in the handpiece memory minimum and maximum drive frequency fields 122 and 124, respectively. A PID coefficient field 230 contains filtering coefficients for the control signals that for the tip may be more specific than the data in handpiece PID coefficient field 126. A tip use history field 232 contains data regarding the use of the tip. Console processor 96 through the memory reader 102 is able to write data to field 232.

Tip memory also contains a target frequency field 234 and an impedance adjustment coefficient field 236. Target frequency field 234 contains data representative of a frequency $\omega_{target}$ that is within the frequency range of the drive signals applied to the handpiece. More particularly frequency $\omega_{target}$ is a frequency that is within the range of drive frequencies of the handpiece at which, when the tip is under load at which the mechanical reactance is at a minimum. It should be understood that the load to which the tip exposed varies between procedures and even within a single procedure. This means that between procedures and within a procedure the frequency at which the mechanical reactance of the handpiece is at a minimal point not constant. Frequency $\omega_{target}$ is therefore a frequency within the normally expected range at which the reactance minimal point for the handpiece load is expected. Coefficient field 236 contains the above-described coefficient m that defines the change of the reactance over frequency.

A system of this disclosure to which handpiece 190 is attached is driven in the same generally manner in which the handpiece 32 is driven. Nevertheless, there are some difference in the process steps as outlined in FIGS. 6A and 6B. In step 142 the control processor 96 does more than just read the data in the handpiece memory 58. Also in step 142 the control processor reads the data in the tip memory 214.

Not shown are steps in which based on the data in the handpiece memory 58 and tip memory 214 in which the processor determined based on these data whether or not the system can vibrate the tip 48. Data indicating that it is inappropriate for the system to vibrate the tip include data indicating the tip has been used beyond its designed lifecycle. Other data indicating that the system should not vibrate the tip include identification data from the handpiece and tip that collectively indicate the tip is not one which the handpiece is intended to vibrate. If it is inappropriate for the system to in the current configuration drive the tip, the control processor 96 typically causes information to be presented on the display 108 indicating why the console will not source a drive signal to the handpiece 190. In some versions of the disclosure, this information is only presented as a warning. After this information is presented, the practitioner is still given the opportunity to actuate the handpiece.

In step 148, the processor 94 sets the target current $i_M^{TARGET}$ based on maximum current value retrieved the tool memory 214. The frequency range of the drive signals may be set based on the range of frequencies also retrieved from memory 214.

A further change in how the characteristics of the drive signal are determined occurs when step 164 is executed. In this version of the disclosure, the control processor 96 does not use the evaluation of Equation (11) to determine if the mechanical components of the handpiece are resonance. Instead, processor uses the following formula for evaluating whether or not the mechanical components of the handpiece are in resonance is as follows:

$$-\text{Re}\left\{\frac{j\omega V_S C_O}{i_S - j\omega V_S C_O}\right\} + m(\omega - \omega_{target}) = 0 \quad (15)$$

Here $\omega_{target}$ is the target resonant frequency read from tip memory field 234. Coefficient m is the coefficient that set the slope for establishing the virtual impedance as a function of frequency. This is the coefficient read from tip memory field 236. Variables m and $\omega_{target}$ thus define the zero crossing and slope of the reactive components of the virtual impedance as represented by plot 185 in FIG. 11. With the addition of the $m(\omega-\omega_{target})$ component, the scalar on the left side of FIG. 15) in comparison to the ratio of Equation (11) can be considered a modified ratio.

The inclusion of the virtual impedance into the evaluation of step 164, ensures that, if there are plural zero crossings of the reactance of the real components of the mechanical components of the reactance within the frequency range of the drive signals, the evaluation will still indicate relative to the desired resonant frequency if the drive signal needs to be decreased or increased. Thus, using the example of plot 186, should the evaluation of this version of step 164 test negative it clearly means that to drive the signal into resonance the frequency must increase. Similarly, if the evaluation tests positive, the frequency of the drive signal clearly must be decreased.

This version of the disclosure is also useful in the event the practitioner wants to first place the tip head 52 against tissue and then actuate the handpiece 32. In this situation, the handpiece and tip when actuated, are already under load. Owing to their mechanical properties, some tips have the characteristic that, when started under load, the resistance of the load immediately damps vibration to the level at which there are essentially no vibrations. When a handpiece and tip is in the condition, the system can essential be considered in a stall state. When the system is in this state the reactance of the mechanical components of the handpiece is essentially constant over the range of drive frequencies. Essentially the mechanical resistive component of the impedance becomes significantly greater than the mechanical equivalents of the inductive and capacitive impedance. This would mean for example that changes in reactance with frequency as represented by plot 184 would be difficult to detect.

Thus in versions of the disclosure where this condition exists the adjustment component of Equation (16) above becomes the primary component of the ratio that varies with frequency. Thus should a handpiece and tip be stalled, the processor, upon the execution of step 164 would still obtain some indication regarding how close the drive frequency is to the drive frequency needed drive the tip at the under load resonant frequency. In practice, what typically happens when the system is in this condition is that the processor increases the frequency of the drive signal. This increase in frequency of the drive signal causes the handpiece drivers and tip to vibrate at a frequency that causes the handpiece to leave the stall state.

It should be appreciated that it may not be necessary to factor a virtual impedance for all tips that may be incorporated into the system of this disclosure. For a tip for which no such adjustment is required, the impedance adjustment coefficient m is set to zero. This results in Equation (15) reducing back down to Equation (11).

In the fourth alternative version of this disclosure, the addition of this virtual impedance is used to regulate the setting of the frequency of the drive signals so the drive signals are at the anti-resonant frequency of the impedance of the mechanical components of the handpiece. Thus, Equations (13) and (15) are combined as follows:

$$-\text{Re}\left\{\frac{j\omega V_S C_O}{i_S - j\omega V_S C_O}\right\} + m(\omega - \omega_{target}) = 1 \quad (16)$$

In still other versions of the disclosure, the modified ratio on left sides of Equations (15) and (16) may be compared to target ratios that are representative of frequency between the resonant and the anti-resonant frequency.

VI. Fourth Alternative Means of Drive Frequency Control

In still another version of this disclosure only the frequency of the drive signal is adjusted. In this version of the disclosure the frequency of the drive signal is adjusted to both apply a drive signal that is at or near the resonant frequency of the mechanical components of the handpiece and at a current level that is at or near the desired target for the equivalent of current that should be applied to the mechanical components of the handpiece.

Figure 15A:
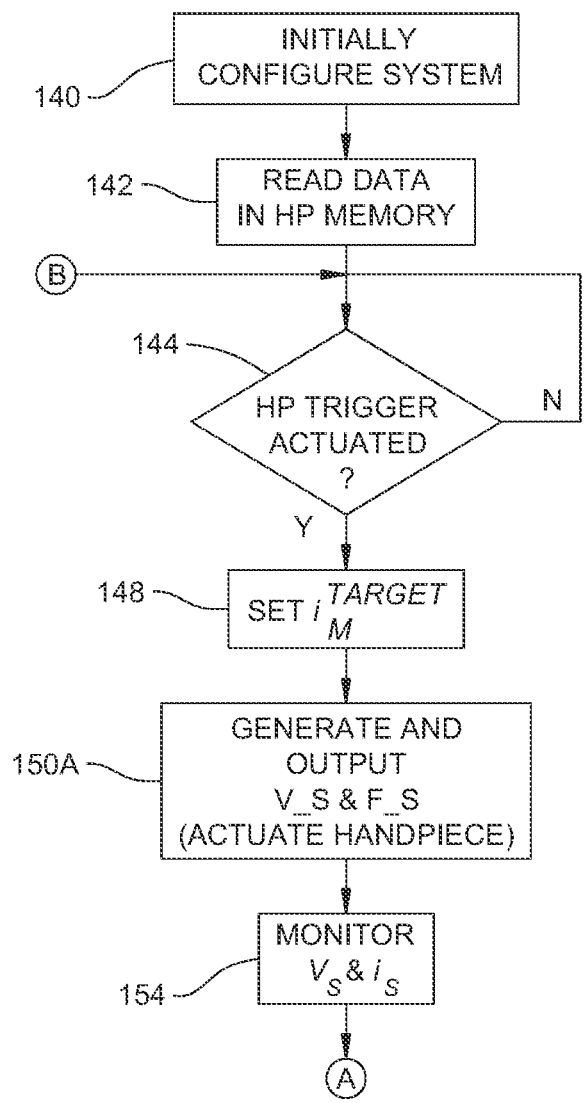
FIGS. 15A and 15B collectively form a flow chart that depicts alternative process steps for regulating an ultrasonic surgical tool system of this disclosure.
Figure 15B:
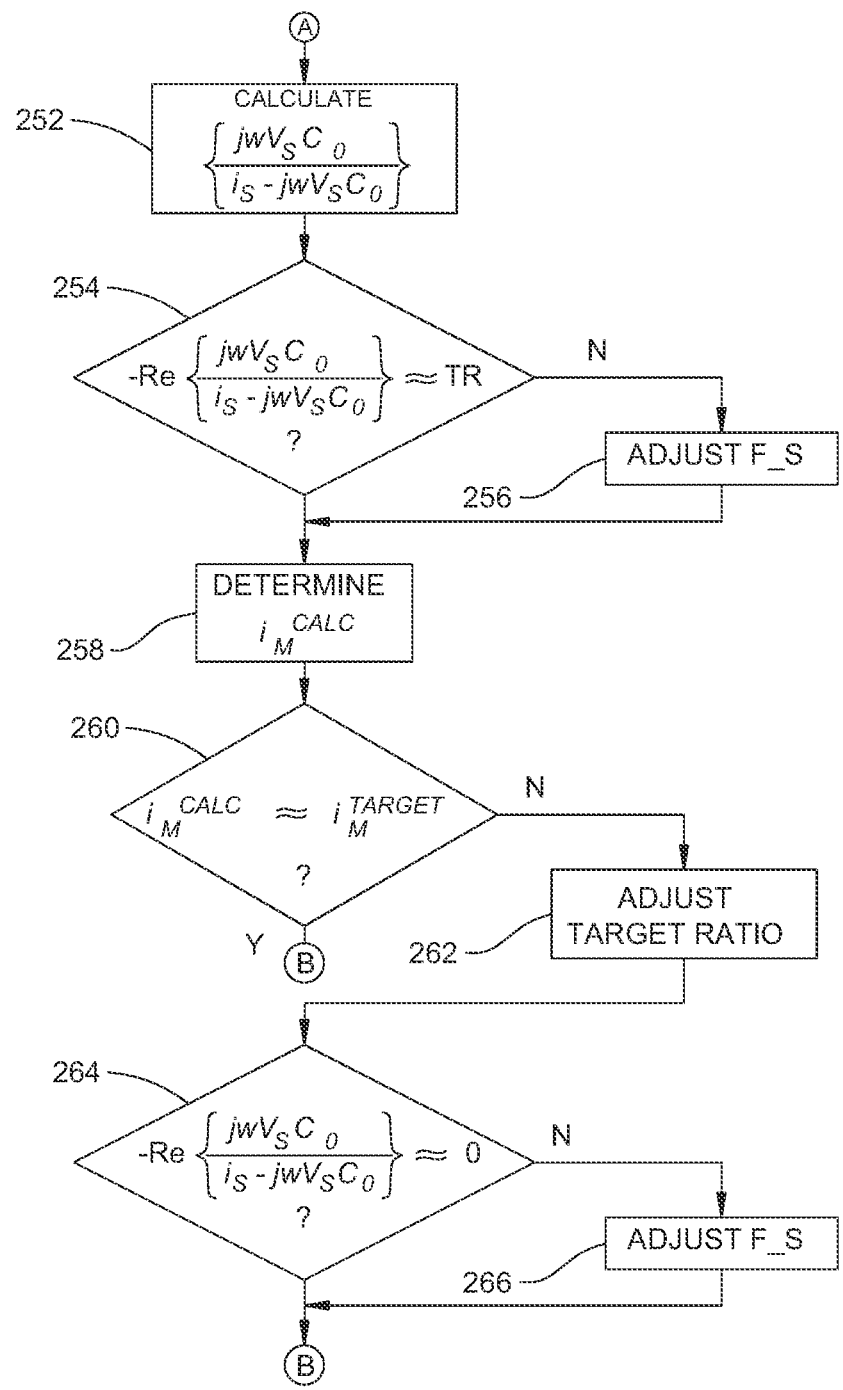

This version of the disclosure is understood by reference to the flow charts of FIGS. 15A and 15B. In this version of the disclosure steps 140, 142, 144, 148 and 154 are performed as substantially the same as described above with respect to the process represented by the flow chart of FIGS. 6A and 6b. In this version of the disclosure when the handpiece is initially actuated a step 150A, which is an alternative to previously described step 150, is executed when the handpiece is initially actuated. In step 150A processor 96 outputs a VOLTAGE_SET signal that is representative of the highest voltage that should be applied to the handpiece. Processor 96 also generates and outputs the FREQUENCY_SET signal. The same process used to determine the initial FREQUENCY_SET signal in step 150 can be used in step 150A to output the same signal in step 150A.

After step 154 is executed, in this method of the disclosure in a step 252 the processor calculates the ratio of the current flow through the drivers 40 to the equivalent current flow through the mechanical components of the handpiece, the ratio of left side of Equation (11). In a step 254 this ratio is compared to a target ratio (TF). Initially, the target ratio is a scalar value representative of the desired target frequency of the drive signal relative to the mechanical components of the handpiece. For example, if it is desired to drive the mechanical components of the handpiece at the resonant frequency, the initial target ratio is zero (0). If it desired to drive the mechanical components of the handpiece at the anti-resonant frequency, the initial target ratio is unity (1). The initial target ratio may be between these values. This will be the case if it is desired to drive the tip at a frequency at which the mechanical components of the handpiece have a responsiveness between the responsiveness at the resonant frequency and the responsiveness at the anti-resonant frequency.

Based on this comparison, if necessary, the frequency of the drive signal is selectively reset, step 256. This analysis and resetting of the FREQUENCY_SET signal are analogues to the analysis and frequency resetting of steps 164 and 166.

After step 254 and, if necessary step 256, are executed, in a step 258, the processor determines the equivalent current flow through mechanical components of the handpiece, current $i_M^{CALC}$. Step 258 is analogues to step 156. In a step 260 this calculated current is compared to the target current, current $i_M^{TARGET}$. Step 260 is analogues to step 158.

If the calculated current is relatively close to the target current, processor 96 has determined that the system is in a situation in which the drive signal is at a frequency which is substantially equal to the desired target frequency for the handpiece mechanical components and the equivalent current through these components is substantially equal to the target of this equivalent of current. If the system is in this state, the processor loops back to step 144. This loop back is analogues to the loop back to step 144 performed after step 164 or step 166 is executed.

As a result of the execution of step 260 it may be determined that there is a substantial difference between the calculated current and the target current. In many situations this is because the calculated current is higher than the target current. If the system of this disclosure is in this state, in a step 262 the processor adjusts the value of the target ratio. This new ratio is $TR^{ADJ}$. This is because the subsequent resetting of the drive frequency away from the target drive frequency will result in a like reduction in the equivalent of current applied to the mechanical components of the handpiece.

In a step 264 the ratio of the current through the drivers over the equivalent of current flow through the mechanical components of the handpiece compared to the adjusted target ratio. Most likely, the comparison will indicate that actual ratio is substantially different than the adjusted target ratio. In this situation, the processor, in a step 266, adjusts the FREQUENCY_SET signal. The FREQUENCY_SET signal is reset to cause the new drive signal to be closer to that needed to cause the equivalent of current applied to the mechanical components of the handpiece to reset to a level approaching the target for this equivalent current. If the differences in the initial target current and the adjusted target current are marginal, step 266 may not be executed.

After the execution of step 264 and sometimes after the execution of step 262, processor 96 loops back to the execution of step 144.

This version of the disclosure sources a drive signal to the handpiece that is at a frequency close to the desired target frequency for the handpiece and that results in the equivalent of current applied to the mechanical components of the handpiece close to the target for this current flow without having to set the potential of the drive signal.

VII. Alternative/Additional Means of Obtaining Driver Capacitance

In alternative versions of the disclosure, internal to the control console 64 is a circuit able to measure the capacitance $C_O$ of the at least one piezoelectric driver. For example, capacitance can be obtained by outputting a drive signal that is swept over a range of frequencies. During this time period measurements of $V_S$ and $i_S$ are generated for the drive signals having different frequencies. Based on these data, processor 96 mathematically determines driver capacitance $C_O$.

System 30 of this disclosure can be configured to perform this capacitance determining process so as to eliminate the need to provide the handpiece with a memory that includes data describing driver capacitance. In these versions of the disclosure, the system determines drive capacitance as part of step 140, the initial configuring of the system.

There are also reasons to provide system 30 with this ability to determine driver capacitance even when the system is able to obtain from a memory associated with the handpiece the data describing the capacitance value of the driver. One reason for which it is desirable to provide the system with this ability and to have the system perform this process is to determine the operating state of the handpiece. Specifically, the system can be configured to perform this step and compare the processor generated determination of driver capacitance with the capacitance value obtained from the handpiece memory, the value obtained in step 142. If these capacitance values are not substantially equal, the processor interprets this difference as indicating that the handpiece may be in a malfunctioning state. This malfunction could occur due to the driver having suffered some type of damage. The processor will then assert a message indicating that the handpiece may not be functioning properly. The practitioner can use this information to determine whether or not it is appropriate to proceed with the procedure using this particular handpiece.

In both constructions of the disclosure, the system may further be configured to determine driver capacitance even after the procedure has started. As mentioned above, driver capacitance is, for the purposes of supplying the drive signal according to this disclosure, substantially constant. Nevertheless, there can be situations in which over time during the procedure, driver capacitance can change. For example, if the handpiece is used for an extended period of time, 10 minutes or more, the handpiece, including the drivers 40 may be subjected due to frictionally induced heating. This heating is the result of the repetitive expansions and contractions of the drivers 40. The temperature change of the handpiece may result in a change in the driver capacitance. Accordingly, even when the initial capacitance is read from the handpiece memory 58, the system may periodically execute the process to determine driver capacitance.

In this construction of the disclosure, if the determined driver capacitance is within a set range of the previous capacitance, processor 96 uses this newly determined driver capacitance as the variable driver capacitance $C_O$ to set the characteristics of the drive signal. However, there may be a situation when the newly determined driver capacitance is outside of the set range relative to the previous driver capacitance. Processor 96 can be set to interpret the system 30 being in this state as an indication that the handpiece 32 has entered a malfunctioning state. If the processor 96 makes this determination, the processor causes a message to be displayed indicating that the handpiece may be in this state.

VIII. Alternative Model of the Impedance of the Mechanical Components of the Handpiece In an alternative construction of the disclosure, the model of the current applied to the drivers 40 and the equivalent of current applied to the mechanical components of the handpiece may be based on alternative models of the resistance, inductance and capacitance of these components.

Figure 14:
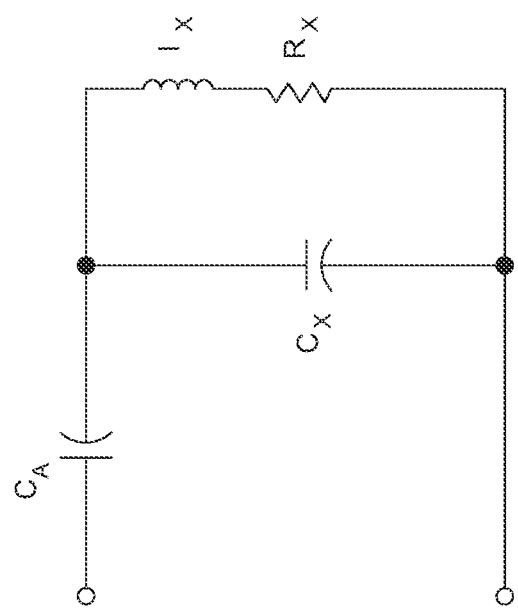
FIG. 14 represents an alternative model of the impedance of the handpiece drivers and the equivalent impedances of the mechanical components of the handpiece.

FIG. 14 depicts one alternative model of the arrangement of the components of the handpiece that present impedance to the current and equivalent applied current. In this model the capacitance has two components, a combined capacitance $C_A$ and blended capacitance $C_X$. Each of these capacitances is a function of both the driver capacitance and the equivalent capacitance of the mechanical components of the handpiece 40 as represented by Equations (14) and (15)

$$C_A = C_O + C_M \quad (17)$$

$$C_X = \frac{C_O^2}{C_M} + C_O \quad (18)$$

The inductance is a blended inductance $L_X$. This inductance is a function of the equivalent inductance of the mechanical components of the handpiece, the equivalent capacitance of these components and the driver capacitance. Equation (19) is one means to determine blended inductance:

$$L_X = L_M \left( \frac{C_M}{C_O + C_M} \right)^2 \quad (19)$$

Resistance is a blended resistance Rx. As indicated by Equation (17) blended resistance is a function of the equivalent resistance of the mechanical components of the handpiece, equivalent capacitance of these components and the driver capacitance:

$$R_X = R_M \left( \frac{C_M}{C_O + C_M} \right)^2 \quad (20)$$

This means there is a like change in the equations used to calculate handpiece impedance, the equivalent of current applied to the mechanical components of the handpiece and the real component of the ratio of the equivalent current flow through the mechanical components of the handpiece.

Further while not illustrated, it should be understood that in other models of the equivalent impedance of the handpiece mechanical components two of three impedance contributing components, the resistance, the inductance or capacitance may be in parallel with each other. In this model the third component is in series with the two parallel components.

IX Additional Alternative Versions

The above is directed to specific versions of this disclosure. Some versions of the disclosure may have features different from what has been described. For example, the foregoing features of the different versions of the disclosure can be combined.

The structural features of the disclosure may also differ from what has been described. For example, the post over which the drivers are disposed may be machined with the horn. Likewise other means may be used to measure the voltage across the handpiece and the current through the handpiece. Thus, resistors as opposed to inductors may be employed to perform this signal sensing. In a number of versions of the disclosure insulating discs may not be present between adjacent drivers. Insulating components may be present between the most proximal driver and mass 36 or between the drivers and the horn. The number of drivers may be less than or more than the number of drivers disclosed.

In some versions of the disclosure a signal foot pedal or handswitch is the control member that is used to both control the on/off state of the handpiece and magnitude of the drive signal applied to the handpiece.

Likewise the electrical components of the system may be different from what has been described. For example, some versions of the control console may not include a Class-D amplifier. In one alternative version of the disclosure, the signal output by the power supply is output to a Class-A amplifier. In one embodiment of this version of the disclosure, the processor 96 still outputs a VOLTAGE_SET signal to the power supply 68 to establish the peak voltage of the drive signal. Processor 68 also outputs a variable frequency sine wave signal to the amplifier as the FREQUENCY_SET signal. The amplifier, based on this FREQUENCY_SET signal, selectively amplifies the signal from the power supply so as to source a drive signal that has the desired frequency. In still other embodiments of this version of the disclosure, the power supply outputs a DC signal at a fixed potential. The processor outs a sine wave that varies in both frequency and peak-to-peak voltage. This signal is thus a combined VOLTAGE_SET signal and FREQUENCY_SET signal. This sine wave is applied to the amplifier. Based on this signal the amplifier selectively amplifies the constant signal from the power signal to produce the selected drive signal. In these versions of the disclosure there may not be a need to filter the drive signal output by the amplifier prior to sourcing the signal to the handpiece 32.

The process steps may be performed in a sequence different from what has been described. Thus, in regard to the version of the disclosure described with respect to the flow chart of FIGS. 6A and 6B, the system can be configured to adjust the frequency of the drive signal before adjusting the voltage of the drive signal. In the version of the disclosure described with respect to FIG. 15A-15C, one of the comparison of the ratio of current flow through the drivers 40 to the equivalent of current flow applied to the mechanical components of the handpiece to the target frequency may be omitted. It is understood that in this version of the disclosure as a result of the execution of steps 260 and 262, the ratio is compared to a target ratio that is almost always being adjusted.

Likewise there may be changes in control algorithms. For example, the component of the algorithm used to modify the ratio between the current sourced the handpiece drivers 40 and the equivalent of current applied to the mechanical components of the handpiece may not always be a first order difference between the target and actual frequencies. In some versions of the disclosure second order or higher order differences between these two frequencies may be used to produce the component that modifies the basic ratio. In other versions of the disclosure, within a first range of the difference in frequencies, the component is based on one order of the difference in these frequencies. Within a second range of the difference in these frequencies the component is based on a second order of difference in frequencies. Likewise in some versions of the disclosure the component throughout a range of difference in frequencies is based on a constant order of difference in frequencies. In this version of the disclosure the coefficient used to determine the modification component may vary as a function of the difference in frequencies.

Therefore, it is the goal of the appended claims to cover all such modifications and variations that come within the true spirit and scope of this disclosure.

What is claimed is:

1. A system for vibrating a tip of an ultrasonic instrument, the ultrasonic instrument having at least one driver to which an AC drive signal is applied to vibrate the tip and at least one memory device storing data indicative of a maximum equivalent of current that should be applied to mechanical components of the instrument, the system comprising:
a control console for generating the AC drive signal that is applied to the at least one driver of the ultrasonic instrument; and
a foot pedal connected to the control console,
wherein the control console is configured to:
read the maximum equivalent of current data from the at least one memory device of the ultrasonic instrument;
responsive to the foot pedal being depressed, determine an extent of the depression of the foot pedal;
calculate a target equivalent of current to be applied to the mechanical components of the instrument based on the read maximum equivalent of current data and the extent of the depression of the foot pedal; and
set a characteristic of the AC drive signal based on the calculated target equivalent of current.

2. The system of claim 1, wherein the characteristic of the AC drive signal set based on the calculated target equivalent of current is a voltage level of the AC drive signal.

3. The system of claim 1, wherein the at least one memory device of the ultrasonic instrument stores data indicative of a capacitance of the at least one driver, and the control console is configured to:
read the capacitance data from the at least one memory device of the ultrasonic instrument; and
at least upon initial activation of the ultrasonic instrument, set the characteristic of the AC drive signal based on the read capacitance data and the calculated target equivalent of current.

4. The system of claim 3, wherein the control console is configured to, at least upon initial activation of the ultrasonic instrument, set a frequency of the AC drive signal based on the read capacitance data.

5. The system of claim 3, wherein the control console is configured to:
after setting the characteristic of the AC drive signal based on the read capacitance data and the calculated target equivalent of current, determine the capacitance of the at least one driver by setting the frequency and voltage of the AC drive signal; and
setting the characteristic of the AC drive signal based on the determined capacitance and the calculated target equivalent of current.

6. The system of claim 3, comprising the ultrasonic instrument coupled to the control console, the ultrasonic instrument including:
a handpiece including the at least one driver and a handpiece memory storing the capacitance data; and
a sleeve disposed over the tip and including an open distal end through which the tip extends, a conduit for flowing irrigating fluid down the sleeve and out the open distal end during operation of the ultrasonic instrument to vibrate the tip, and a tip memory storing the maximum equivalent of current data,
wherein the control console is configured to read the capacitance data from the handpiece memory and read the maximum equivalent of current data from the tip memory.

7. The system of claim 1, wherein the control console comprises a transformer including a primary winding and a secondary winding across which the AC drive signal is induced by a signal applied to the primary winding, the transformer also including a coil for measuring a voltage of the AC drive signal, wherein the control console is configured to set the characteristic of the AC drive signal applied to the at least one driver of the ultrasonic instrument based on the measured voltage of the AC drive signal and the calculated target equivalent of current.

8. The system of claim 7, wherein the control console comprises a conductor extending from the secondary winding for supplying the AC drive signal to the instrument and a coil disposed in proximity to the conductor for measuring a current of the AC drive signal, and the control console is configured to set the characteristic of the AC drive signal applied to the at least one driver of the ultrasonic instrument based on the measured voltage of the AC drive signal, the measured current of the AC drive signal, and the calculated target equivalent of current.

9. The system of claim 1, wherein the at least one memory device of the ultrasonic instrument stores data indicative of PID coefficients for regulating the AC drive signal, and the control console is configured to:
read the PID coefficient data from the at least one memory device of the ultrasonic instrument; and
set the characteristic based on the read PID coefficient data and the calculated target equivalent of current.

10. The system of claim 9, wherein the control console is configured to set a frequency of the AC drive signal based on the read PID coefficient data.

11. A method for regulating an AC drive signal sourced from a control console to an ultrasonic instrument to vibrate a tip of the ultrasonic instrument, the ultrasonic instrument having at least one driver to which an AC drive signal is applied to vibrate the tip and at least one memory device storing data indicative of a maximum equivalent of current that should be applied to mechanical components of the instrument, the control console being connected to a foot pedal, the method comprising:
reading, by the control console, the maximum equivalent of current data from the at least one memory device of the ultrasonic instrument;
determining, by the control console, a depression of the foot pedal and an extent of the depression;
calculating, by the control console, a target equivalent of current to be applied to the mechanical components of the instrument based on the read maximum equivalent of current data and the extent of the depression of the foot pedal; and
setting, by the control console, a characteristic of the AC drive signal based on the calculated target equivalent of current.

12. The method of claim 11, comprising setting a voltage level of the AC drive signal based on the calculated target equivalent of current.

13. The method of claim 11, wherein the at least one memory device of the ultrasonic instrument stores data indicative of a capacitance of the at least one driver, and comprising:
reading, by the control console, the capacitance data from the at least one memory device of the ultrasonic instrument; and at least upon initial activation of the ultrasonic instrument, setting, by the control console, the characteristic of the AC drive signal based on the read capacitance data and the calculated target equivalent of current.

14. The method of claim 13, comprising, at least upon initial activation of the ultrasonic instrument, setting, by the control console, a frequency of the AC drive signal based on the read capacitance data.

15. The method of claim 13, comprising:
after setting the characteristic of the AC drive signal based on the read capacitance data and the calculated target equivalent of current, determining the capacitance of the at least one driver by setting the frequency and voltage of the AC drive signal; and
setting the characteristic of the AC drive signal based on the determined capacitance and the calculated target equivalent of current.

16. The method of claim 13, wherein the ultrasonic instrument comprises a handpiece and a sleeve disposed over the tip, the handpiece including the at least one driver and a handpiece memory storing the capacitance data, and the sleeve including an open distal end through which the tip extends, a conduit for flowing irrigating fluid down the sleeve and out the open distal end during operation of the ultrasonic instrument to vibrate the tip, and a tip memory storing the maximum equivalent of current data, the method comprising:
reading, by the control console, the capacitance data from the handpiece memory; and
reading, by the control console, the maximum equivalent of current data from the tip memory.

17. The method of claim 11, wherein the at least one memory device of the ultrasonic instrument stores data indicative of PID coefficients for regulating the AC drive signal, and comprising:
reading, by the control console, the PID coefficient data from the at least one memory device of the ultrasonic instrument; and
setting, by the control console, the characteristic of the AC drive signal based on the read PID coefficient data and the calculated target equivalent of current.

18. The method of claim 16, comprising setting, by the control console, a frequency of the AC drive signal based on the read PID coefficient data.

\* \* \* \* \*